(12) United States Patent
Fraker et al.

(10) Patent No.: US 9,175,254 B2
(45) Date of Patent: *Nov. 3, 2015

(54) ENHANCED OXYGEN CELL CULTURE PLATFORMS

(71) Applicant: University of Miami, Miami, FL (US)

(72) Inventors: Christopher A. Fraker, Miami, FL (US); Juan Dominguez-Bendala, Miramar, FL (US); Camillo Ricordi, Miami, FL (US); Luca Inverardi, Miami, FL (US)

(73) Assignee: University of Miami, Miami, FL (US)

( * ) Notice: Subject to any disclaimer, the term of this patent is extended or adjusted under 35 U.S.C. 154(b) by 162 days.

This patent is subject to a terminal disclaimer.

(21) Appl. No.: 14/047,218

(22) Filed: Oct. 7, 2013

(65) Prior Publication Data

US 2014/0099717 A1   Apr. 10, 2014

Related U.S. Application Data

(63) Continuation-in-part of application No. 11/775,012, filed on Jul. 9, 2007, now Pat. No. 8,551,770.

(60) Provisional application No. 60/819,153, filed on Jul. 7, 2006.

(51) Int. Cl.
| | |
|---|---|
| C12Q 1/02 | (2006.01) |
| C12N 1/00 | (2006.01) |
| C12M 1/04 | (2006.01) |
| C12M 1/32 | (2006.01) |
| C12M 1/00 | (2006.01) |
| C12M 1/12 | (2006.01) |

(52) U.S. Cl.
CPC ............... *C12M 23/24* (2013.01); *C12M 23/12* (2013.01); *C12M 23/20* (2013.01); *C12M 25/04* (2013.01); *C12M 29/04* (2013.01)

(58) Field of Classification Search
CPC ...... C12M 23/12; C12M 23/20; C12M 29/04; C12M 23/24; C12M 25/04
See application file for complete search history.

(56) References Cited

U.S. PATENT DOCUMENTS

| | | | | |
|---|---|---|---|---|
| 4,435,508 | A * | 3/1984 | Gabridge | 435/297.5 |
| 4,748,124 | A * | 5/1988 | Vogler | 435/401 |
| 4,781,799 | A * | 11/1988 | Herbert et al. | 205/73 |
| 5,066,683 | A * | 11/1991 | Dillon et al. | 521/54 |
| 5,366,893 | A * | 11/1994 | Stevens et al. | 435/297.5 |
| 5,449,617 | A | 9/1995 | Falkenberg et al. | |
| 5,693,537 | A * | 12/1997 | Wilson et al. | 435/401 |
| 5,856,245 | A * | 1/1999 | Caldwell et al. | 442/76 |
| 5,863,792 | A * | 1/1999 | Tyndorf et al. | 435/297.5 |
| 7,379,765 | B2 * | 5/2008 | Petisce et al. | 600/345 |
| 8,551,770 | B2 * | 10/2013 | Fraker | C12M 23/04 210/500.21 |
| 2002/0045672 | A1 * | 4/2002 | Harris et al. | 521/61 |
| 2005/0106717 | A1 * | 5/2005 | Wilson et al. | 435/297.5 |
| 2006/0258761 | A1 * | 11/2006 | Boock et al. | 521/50 |

* cited by examiner

*Primary Examiner* — William H Beisner
*Assistant Examiner* — Danielle Henkel
(74) *Attorney, Agent, or Firm* — Novak Druce Connolly Bove + Quigg LLP

(57) ABSTRACT

Provided is a cell culture apparatus for culturing cells, that provides enhanced oxygen delivery and supply to cells without the need for stirring or sparging. Oxygen diffusion occurs on both sides of the culture vessel, top and bottom. A gas-permeable membrane that includes perfluorocarbons or fluorocarbon derivatives (e.g., fluorinated silane, partially fluorinated silane) in its composition allows for the rapid, enhanced and uniform transfer of oxygen between the environment of cells or tissues contained in the cell culture container apparatus and the atmosphere of the incubator in which the cell culture apparatus is incubated.

19 Claims, 15 Drawing Sheets

FIG. 2A-D

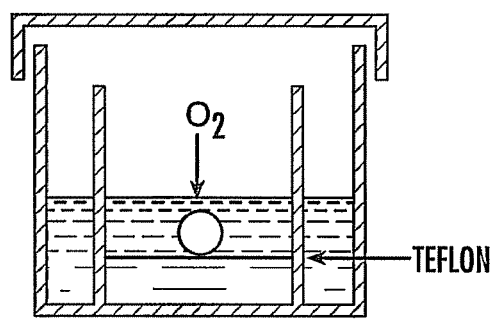
STANDARD CULTURE
FIG. 5A
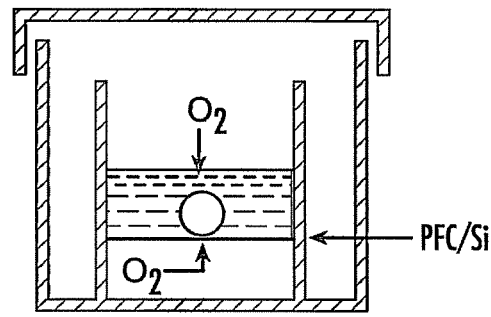
PFC/SILIC ONE DEVICES
FIG. 5C
FIG. 5B
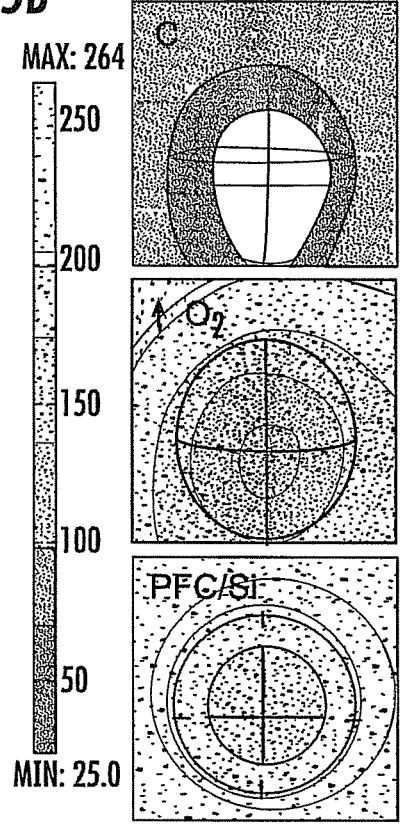

ENHANCED OXYGEN CELL CULTURE PLATFORMS

CROSS-REFERENCE TO RELATED APPLICATIONS

The present application is a continuation-in-part of U.S. non-Provisional patent application Ser. No. 11/775,012, filed on Jul. 9, 2007, entitled ENHANCED OXYGEN CELL CULTURE PLATFORMS, which claims priority of U.S. Provisional Patent Application No. 60/819,153, filed Jul. 7, 2006, entitled ENHANCED OXYGEN CELL CULTURE, the contents of both of which are incorporated herein by reference in their entireties.

FIELD OF THE INVENTION

The invention generally relates to an apparatus and methods for growing cells or tissue culture in vitro. More particularly, the present invention relates to a cell culture apparatus containing at least one gas permeable membrane which allows rapid, enhanced and uniform transfer of oxygen between the environment of cells contained in the cell culture container apparatus and the atmosphere of the incubator in which the cell culture apparatus is incubated.

BACKGROUND

In eukaryotic cell culture systems, the culture of the cells is generally under conditions of controlled pH, temperature, humidity, osmolarity, ion concentrations, and exchange of gases. Regarding the latter, oxygen and carbon dioxide ($CO_2$) are of particular importance to the culturing of cells. In a typical eukaryotic cell culture system, an incubator is provided in which $CO_2$ is infused to maintain an atmosphere of about 5% $CO_2$ within the incubator. The $CO_2$ interacts with the tissue culture medium, particularly its buffering system, in maintaining the pH near physiologic levels. Conventional cell culture containers comprise tissue culture flasks, tissue culture bottles, and tissue culture plates. Entry of $CO_2$ from the incubator atmosphere into a tissue culture plate generally involves a loosely fitting cover which overhangs the plate in excluding particulate contaminants from entering the plate chamber(s), but allows gas exchange between the incubator atmosphere and the atmosphere within the tissue culture plates. Similarly, for a tissue culture flasks or bottle, a loosely fitting cap excludes particulate contaminants from entering the chamber of the flask or bottle, but allows gas exchange between the incubator atmosphere and the atmosphere within the flask or bottle. More recently, a cap is provided with a gas permeable membrane or filter, thereby allowing for gas exchange with a tightly fitting cap.

In addition to $CO_2$, the culturing of cells is dependent upon the ability to supply to the cells a sufficient amount of oxygen necessary for cell respiration and metabolic function. The supply of oxygen for cell respiration in conventional cell culture containers is in the header space of the container, e.g., the void space in the container that is above the surface of the tissue culture medium. Efforts to increase oxygen concentration to the cultured cells includes mechanical stirring, medium perfusion or aeration, increasing the partial pressure of oxygen, and/or increasing the atmospheric pressure. Thus, in conventional cell culture containers the volume or surface provided for gas exchange, as relative to the volume or surfaces of the whole container, is either inefficiently used and/or results in limiting the rate of gas exchange or in the equilibration of gases. This is even more noticeable in small-scale cultures (15 ml or less) in which rate of cell growth, cell densities, and total cell numbers, are frequently low due to space, surface area, and gas exchange limitations. There is also evidence that suboptimal oxygen levels across precursor tissues in vitro result in a lower degree of differentiation.

Varying levels of oxygen in cultured embryonic stem cells, for instance, determine whether they will proliferate or differentiate. A clear relation between oxygenation and differentiation has also been observed in endothelial and mesenchymal stem cells. In another in vitro system, we have shown that pancreatic beta cell differentiation in vitro is greatly enhanced by oxygen. This is consistent with the observation that the second and most significant wave of beta cell specification during embryonic development (secondary transition) is concurrent with the initiation of blood flow within the pancreatic buds. There is, therefore, a need in the art to provide tissue culture systems wherein oxygen delivery is enhanced, or adjusted depending on the culture setting, proliferation, differentiation and/or viability.

SUMMARY

A system/apparatus is described that provides enhanced delivery of oxygen to cells in conventional static culture platforms through the modification of conventional culture systems in that oxygen diffusion occurs on both sides of the culture vessel, top and bottom. A gas permeable membrane composition is further provided.

In typical culture vessels, made of stable, relatively gas impermeable plastics such as polystyrene or polypropylene, cells rest upon the bottom plastic surface and are covered by a given medium depth to allow for adequate oxygenation from air above the medium layer. This system is far from ideal in that the cell/media layer rapidly forms sharp oxygen gradients depending on the seeding density and the oxygen consumption rate of the cultured tissue. This leads to the development of anoxic core regions in cultured cells when they are of a diameter greater than approximately 400 micrometers or when they are cultured in seeding densities that exceed 1-3% of the culture flask surface area. The result is an increased cost and inefficiency in culturing large quantities of cells, not to mention the increased risk of contamination due to the manipulation of numerous culture vessels. Also, the effect on cell functionality, viability and differentiation, particularly in cells with significant metabolic activity, such as Islets of Langerhan's, is significantly negative.

In a preferred embodiment, a cell and tissue culture apparatus comprises a tissue culture well comprising a membrane barrier; support members extending from the bottom of the tissue culture well to elevate the tissue culture well; and, a tray or tissue culture flask comprising the tissue culture well. Support members can also be on the side or top of the well, or in any other way so that the bottom barrier is elevated and air can flow through it. The tissue culture well comprises an upper and lower opening; and a gas permeable, liquid non-permeable membrane barrier wherein said barrier defines a continuous bottom surface the tissue culture well.

In a preferred embodiment, the membrane barrier comprises a perfluorinated hydrocarbon and silicone composition. Preferably, the perfluorinated hydrocarbon comprises fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, or sulfur hexafluoride.

In another preferred embodiment, the membrane barrier comprises a fluorocarbon derivative and silicone composition. Examples of fluorocarbon derivatives include perfluorotributyl amine, fluorinated silanes and partially fluorinated silanes Other alternative molecules that promote oxygen exchange and could be used in the formulation of the barrier include, but are not limited to, neuroglobin, hemoglobin and myoglobin.

In a preferred embodiment, the perfluorinated hydrocarbon and silicone composition has a ratio of between about 0.001% v/v perfluorinated hydrocarbon per ml of silicone up to 80% v/v perfluorinated hydrocarbon per ml of silicone. Similarly, a fluorocarbon derivative and silicone composition has a ratio of between about 0.001% v/v fluorocarbon derivative per ml of silicone up to 80% v/v fluorocarbon derivative per ml of silicone.

In another preferred embodiment, the $O_2$ is further enhanced by culturing the cells in various media which allow for a higher $O_2$ uptake. For instance, perfluoro emulsions.

In another preferred embodiment, the membrane barrier comprises at least one material selected from ceramics, polymers, woven substrates, non-woven substrates, polyamide, polyester, polyurethane, fluorocarbon polymers, polyethylene, polypropylene, perfluorinated hydrocarbon, fluorocarbon derivatives, polyvinyl alcohol, hydrogels and silicone.

In another preferred embodiment, the membrane barrier comprises pores of at least about 0.001 μm up to 0.5 μM in size. Preferably, the membrane barrier is at least about 0.01 μM thick up to about 1 mm thick.

In yet another embodiment, the tissue culture well is made from at least one material comprising polypropylene, polystyrene, vinyl, other plastics, metals, alloys, minerals, non-metallic minerals, wood, fibers, cloth and glass. The tray comprising at least one or more tissue culture wells, is made from at least one material comprising polypropylene, polystyrene, vinyl, other plastics, metals, alloys, minerals, non-metallic minerals, wood, fibers, cloth and glass.

The shape, dimensions of the tissue culture well and tray can vary depending on the needs of the user. For example, the tissue culture well can be circular, rectangular and the like. The size of the tissue culture well tissue culture well can be the size of a typical 384 well plate, a typical 96 well tissue culture plate, a typical 24 well tissue culture plate, a 12 well tissue culture plate, a 6 well tissue culture plate and the like. The system can also be in the shape of a tissue culture flask. The barrier can be along the base or side of the flask.

In one aspect of the invention, the tray comprises a lid which allows for gaseous exchange. The system can be incubated in incubators with varying oxygen percentages. For example, incubators with about 1% to 100% $O_2$, and/or hyperbaric chambers The system ensures that the delivery of $O_2$ is continuous, efficient, and enhanced compared to typical tissue culture systems.

In another preferred embodiment, the apparatus is molded into a bag. The bag can be any shape or size depending on the user's requirement, e.g. square, rectangular, circular and the like. The thickness of the membrane r is at least about 0.01 μM thick up to about 1 mm thick. Examples of sizes of the bag include but not limited to: 200 mL bag: 17.53 cm length×11.43 cm width (6.9 in. length×4.50 in. width); 150 mL bag: 14.86 cm length.times.7.62 cm width (5.85 in. length-.times.3.0 in. width); bag: 8.84 cm length.times.7.04 cm width.times.0.74 cm depth (3.48 in. length.times.2.77 in. width.times.0.29 in. depth). In other embodiments the bag comprises more than one chamber, one or more openings and the like.

In another preferred embodiment, a composition comprises a highly permeable silicone matrix impregnated, mixed, combined or cross-linked with a perfluorocarbon or fluorocarbon derivative. Preferably, the perfluorocarbon or fluorocarbon derivative comprises fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, fluorinated silanes, partially fluorinated silanes, or sulfur hexafluoride.

In one embodiment, the perfluorocarbon and silicone composition has a ratio of between about 0.001% v/v perfluorocarbon per ml of silicone up to 80% v/v perfluorocarbon per ml of silicone. Similarly, the fluorocarbon derivative and silicone composition has a ratio of between about 0.001% v/v fluorocarbon derivative per ml of silicone up to 80% v/v fluorocarbon derivative per ml of silicone.

In another preferred embodiment, a method of growing cells or tissue explants in an enhanced oxygen delivery tissue culture apparatus, the method comprises (a) suspending the cells or tissue explants to be cultured in the apparatus of the invention, in an appropriate amount of tissue culture medium to form a suspension; (b) introducing the suspension into an instrument for injecting the suspension into a tissue culture well of the apparatus; and, (c) incubating the cell culture apparatus, containing the suspension of medium and cells, in a cell culture incubator. Preferably, the cells to be cultured are anchorage-dependent cells or anchorage-independent cells. Cultured tissue sections are also contemplated within the scope of the invention.

In another preferred embodiment, the culture system comprising the cells, tissues or organs is incubated in a range of oxygen levels and temperatures. For example, incubators with about 1% to 100% $O_2$, and/or hyperbaric chambers.

In another preferred embodiment, a method to determine the effect of enhanced oxygen delivery and availability to a cell culture, comprises culturing cells in an apparatus comprising: a tissue culture device containing a membrane barrier; support members extending from the bottom, side or top of the tissue culture well to elevate the tissue culture well; and, a tray or culture flask comprising the tissue culture well.

In another preferred embodiment, the apparatus comprises an upper and lower opening; and a gas permeable membrane barrier wherein said barrier defines a continuous bottom surface the tissue culture device. Preferably, the membrane barrier comprises at least one material selected from ceramics, polymers, woven substrates, non-woven substrates, polyamide, polyester, polyurethane, fluorocarbon polymers, polyethylene, polypropylene, perfluorinated hydrocarbon, polyvinyl alcohol, hydrogels and silicone.

In a preferred embodiment, the membrane barrier comprises a perfluorinated hydrocarbon or fluorocarbon derivative and silicone composition. Examples of perfluorinated hydrocarbon or fluorocarbon derivatives include, but are not limited to fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, fluorinated silanes, partially fluorinated silanes, and sulfur hexafluoride.

In another preferred embodiment, an apparatus for the transportation of cells, tissues and organs comprises a culture device containing a membrane barrier; and, a container enclosing the culture device under sterile conditions.

In another preferred embodiment the culture device comprises an upper and lower opening; and a gas permeable membrane barrier wherein said barrier defines a continuous surface of at least one side of the culture device. Preferably, the membrane barrier comprises a perfluorinated hydrocarbon and silicone composition.

In another preferred embodiment the perfluorinated hydrocarbon or fluorocarbon derivative comprises fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, fluorinated silanes, partially fluorinated silanes or sulfur hexafluoride.

In a preferred embodiment, the perfluorinated hydrocarbon and silicone composition has a ratio of between about 0.001% v/v perfluorinated hydrocarbon per ml of silicone up to 80% v/v perfluorinated hydrocarbon per ml of silicone.

In another preferred embodiment, the membrane barrier comprises pores of at least about 0.001 µm up to 1 mm in size.

The culture device, apparatus or system is made from at least one material selected comprising polypropylene, polystyrene, vinyl, other plastics, metals, alloys, minerals, non-metallic minerals, wood, fibers, cloth and glass. The container is made from at least one material comprising polypropylene, polystyrene, vinyl, other plastics, metals, alloys, minerals, non-metallic minerals, wood, fibers, cloth and glass.

In another preferred embodiment, the membrane barrier is at least about 0.01 µM thick up to about 1 mm thick.

As described herein, the term "fluorocarbon derivative" means highly fluorinated molecules that can be commonly referred to as fluorocarbons. Included in the definition of fluorocarbon derivative are fluorinated compounds or partially fluorinated compounds. Examples include fluorinated alkyl silanes and partially fluorinated alky silanes. A fluorinated silane is any compound containing the backbone silane structure (Si) with four bonds where one or more of the bonds, typically with hydrogen, is replaced by a fluorine atom or fluorine containing tail group. Some examples of a fluorinated silane include but are not limited to fluorosilane, perfluoroalkyl silane, triexthoxy fluorosilane and 1H,1H,2H,2H-perfluorooctyltriethoxysilane.

The term "fluorosilane" as used herein means any fluorinated silane with any potential end groups. One example of a fluorosilane is triethoxyfluorosilane, which has three methyl ($CH_3$) groups attached, one fluorocarbon derivative tail (partially fluorinated alkyl) and then the Si backbone.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 2A are neurospheres cultured in high $O_2$ control conditions (48 h). FIG. 2B are neurospheres cultured in PFC/Si dishes, also at high $O_2$ (48 h). These are representative of Control vs. PFC/Si conditions at both standard and high $O_2$ concentrations. Red BrdU staining (indicating proliferation) is shown in control (FIG. 2C) and PFC/Si-cultured neurospheres (FIG. 2D). DAPI (blue) is a nuclear counter-staining. Scale bars (upper and lower rows): 500 µm.

FIG. 5A-5C show enhanced oxygenation in PFC/Si devices. FIGS. 5A and 5C are a schematic representation of the "oxygen sandwich" principle. In standard culture vessels, atmospheric oxygen can reach the tissue only after diffusion through the culture medium. In PFC/Si devices, the sample rests atop a perfluorocarbon-enriched, air permeable silicone membrane, which provides additional oxygenation. FIG. 5B is a COMSOL v.3.2 mathematical modeling of oxygen gradients in pancreatic buds immediately after equilibration (day 0) in standard conditions at 21% oxygen (top), standard conditions at 35% oxygen (middle) and PFC/Si devices at 35% oxygen (bottom). Left, oxygen partial pressure scale (mm Hg), from blue (minimum) to red (maximum). White represents areas with <0.1 mm Hg oxygen (anoxia).

FIG. 6A is a graph showing the volume of pancreatic buds ($m^3$) after three days of culture in each condition (standard control, high oxygen control and PFC/Si), showing a favorable effect of oxygen on cell proliferation. The baseline represents the average volume of buds immediately after harvesting (day 0). Error bars: standard error for each group. FIG. 6B shows in the left column: microphotographs of buds cultured for 3 days in each condition. Scale bar: 400 µm. Right column: immunofluorescent analysis of pancreatic buds (day 3 of culture) with a hypoxyprobe (Chemicon), which detects areas at <10 mm Hg (hypoxia)(green). Blue, DAPI nuclear counter-staining. Scale bar: 500 µm.

FIG. 8A is a graph showing relative qRT-PCR analysis of pancreatic buds cultured in standard conditions (closed bars), high oxygen (striated bars) and PFC/Si devices (grey bars). Values are represented as x-fold increase over the control (=1). Error bars: standard error (7 independent experiments). All values were normalized against 18S RNA (see Methods). FIG. 8B is a graph showing Metamorph® analysis of insulin (left) and glucagon (right) signal in immunostained buds cultured in standard (closed bars), high oxygen (striated bars) and PFC/Si (grey bars) settings. Y axis: x-fold increase over standard control (=1). Error bars: standard error (5 independent experiments). FIG. 8C shows confocal microphotographs of representative sections from e13.5 buds cultured for three days in standard conditions (left), high oxygen (middle) and PFC/Si platforms (right). Insulin (Ins)-positive cells are stained in red and glucagon (Glu)-positive cells in green. Blue: DAPI nuclear counter-staining A white dotted line has been added to highlight the contour of the samples. Scale bar: 100 µm.

FIG. 9A shows total insulin content in each group (standard control, high oxygen control and PFC/Si), represented as the proportion of that found in dorsal pancreatic buds obtained from e16.5 embryos (=1). Error bars: standard error for each group (n=4). FIG. 9B shows gene expression profile of PFC/Si-cultured e13.5 buds, expressed as a percentage of that of freshly isolated e16.5 buds. A dotted line highlights 100% of e16.5 expression. Error bars: standard error for each group (n=4 independent harvests for e16.5 and 7 independent experiments for PFC/Si).

FIG. 10A shows endocrine-to-exocrine ratiometric analysis: Ins1/Amy (Insulin 1 to amylase); Ins1/p48 (Insulin 1 to P48); and Ins1/CPA (Insulin 1 to Carboxypeptidase A). The same ratios were calculated for Insulin 2 (Ins2). FIG. 10B shows β-to-α cell ratiometric analysis: Pax4/Arx; Ins1/Glu (Insulin 1 to Glucagon); Ins2/Glu (Insulin 2 to Glucagon); and Pax4/Pax6. Error bars: standard error for each group.

DETAILED DESCRIPTION

Figure 1:
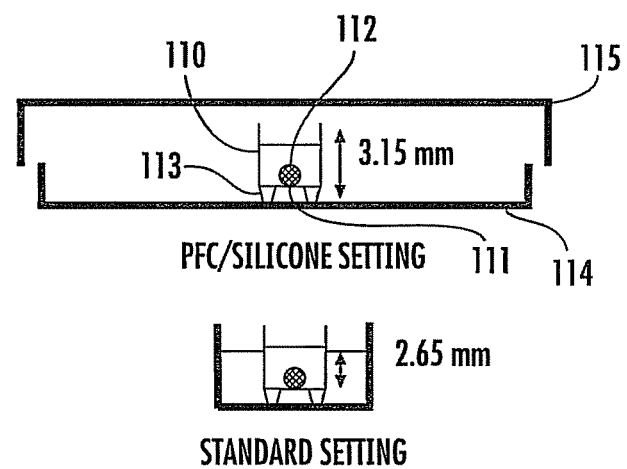
FIG. 1 is a schematic representation illustrating one embodiment of the apparatus of the invention.

An apparatus provides enhanced delivery of oxygen to cells in static culture platforms providing oxygen diffusion on both sides of the culture vessel, top and bottom.

The present tissue culture apparatus/system/device is superior to any typical systems by providing increased oxygen supplies to cells. In typical systems, increased requirements for oxygen are accommodated by mechanical stirring methods and the sparging of gases into the culture. However, both stirring and the sparging of gases can result in damaging cells, thereby decreasing the viability of the culture and the overall efficiency and productivity of the cell and/or tissue culture. Further, direct sparging of cell and tissue cultures with gas can lead to foam production which, is also detrimental to cell viability. On the other hand, just increasing the concentration of oxygen in the incubator has proven insufficient due to the generation of sharp oxygen gradients throughout the sample. The present invention further allows for high density tissue culturing of cells.

Varying levels of oxygen in cultured embryonic stem cells, for instance, determine whether they will proliferate or differentiate. A clear relation between oxygenation and differentiation has also been observed in endothelial and mesenchymal stem cells. In another in vitro system, we have shown that pancreatic beta cell differentiation in vitro is greatly enhanced by oxygen. This is consistent with the observation that the second and most significant wave of beta cell specification during embryonic development (secondary transition) is concurrent with the initiation of blood flow within the pancreatic buds.

In a preferred embodiment, a tissue culture apparatus provides enhanced delivery of oxygen to cells or tissues being cultured. The apparatus or system is superior to conventional culturing systems by providing oxygen diffusion through both sides of the culture vessel, top and bottom. In typical culture vessels, made of stable, relatively gas impermeable plastics such as polystyrene or polypropylene, cells rest upon the bottom plastic surface and are covered by a given medium depth to allow for adequate oxygenation from air above the medium layer. These types of systems are far from ideal in that the cell/media layer rapidly forms sharp oxygen gradients depending on the seeding density and the oxygen consumption rate of the cultured tissue. This leads to the development of anoxic core regions in cultured cells when they are of a diameter greater than approximately 400 micrometers or when they are cultured in seeding densities that exceed 1-3% of the culture flask surface area. The result is an increased cost and inefficiency in culturing large quantities of cells, not to mention the increased risk of contamination due to the manipulation of numerous culture vessels. Also, the effect on cell functionality, viability and differentiation, particularly in cells with significant metabolic activity, such as Islets of Langerhans, is significantly negative.

The tissue culturing apparatus of the invention comprises culture platforms where the bottom surface comprises a thin film silicone layer containing a 10-20% v/v perfluorocarbon or fluorocarbon derivative micellar suspension. In preferred embodiments, the perfluorocarbon micellar suspension ranges from about 0.001% up to 80% v/v, perfluorocarbon or fluorocarbon derivative to silicone. Both silicone and perfluorocarbon have solubility and diffusivities/permeabilities for oxygen which are far greater than either culture medium or plastics. By placing the cells on a highly oxygenated and permeable layer, the tissue cultured is effectively sandwiched by oxygen eliminating the top to bottom gradients present in conventional culture conditions. In this case, the area of lowest oxygenation becomes the middle region of the cell layer rather than the bottom area of the dish, and with modifications in oxygen concentration, this region can be controlled to prevent anoxia.

The apparatus or system is superior to similar culture platforms where the bottom surface comprises a thin silicone layer without perfluorocarbon or fluorocarbon derivative. The advantages of PFC/Si over silicone alone in terms of $O_2$ diffusion were confirmed by direct measurements using non-invasive optical $O_2$ biosensors (See the oxygen transfer studies in the Examples section which follows.). Endocrine differentiation outcomes were also superior in a mouse model of pancreatic development (See the Examples which follow: enhanced oxygenation promotes beta cell differentiation in vitro).

The dimensions of the culture wells or inserts have variable dimensions depending on the desired culturing of tissue sections or cells. For example, if a 24-well type culturing is desired then the wells would have a dimension corresponding to typical 24-well plates.

In another example, is a 96-well plate architecture that exemplifies the general configuration of the current industry-standard format. Its overall height, width, and length are standardized at about 0.560, 3.365, and 5.030 inches, respectively. The plate includes a surrounding skirt, a top surface and an array of wells arranged in twelve rows of eight wells each, to provide 96 identical wells in the plate. For example, the standard micro-titer plates (96 well) bottom surface area is 0.32 cm$^2$. This would translate to a radius of 0.32 cm and the membrane thickness would still be in the micrometer range, e.g. 50-600 µm). The top surface extends between the skirt and the periphery of the wells on the outside of the 96 well matrix. The plates typically are molded of plastics and are provided with transparent covers with drop rings to control water loss by evaporation, while allowing gas exchange and maintaining sterility.

Standardization of the 96-well format has led to the development of a substantial variety of equipment to perform liquid transfers to and from the well chambers, to transmit light through the wells, to read colorimetric or fluorescent changes, or chemiluminescence in individual wells, and many other functions. The liquid transferring equipment is either manually or robotically operated, and much of the equipment used to study the contents of wells is automated and instrumented to record, analyze and manipulate the data. The present invention provides automation-friendly vessels and either a single reservoir or a multi-well base plate that is compatible with the auxiliary equipment designed for the 96- or 384-well format in all aspects.

In another example, the wells or tissue culture inserts have an inner diameter of 1 cm and are about 1 cm in height, holding a maximal volume of about 785 µL. The culture insert bottoms comprise a highly permeable silicone matrix impregnated with perfluorocarbon in a given volume/volume percentage. This combination provides an oxygen reservoir on the basal surface, with no barrier of medium between the cells and the air, as the bottom surface would be impermeable to liquid.

Turning to a general description of the culture apparatus as shown as a schematic illustration in FIG. 1. Reference to the figures is by way of examples and they are by no way limiting the scope of the present invention. The tissue culture well or insert 110 comprises a gas-permeable barrier 111 which provides enhanced delivery of oxygen to cells being cultured 112. The tissue culture well (inserts) further comprises at least two or more members 113 attached to the bottom of the insert which elevate the tissue culture well/insert above the tray 114. The elevating members 113, elevate the tissue culture well/insert 110 about 1 mm to about 3 mm above the tray. The tray comprises a lid 115, typically used in tissue culture to allow for the exchange of gases. The plates typically are molded of plastics and are provided with transparent covers with drop rings to control water loss by evaporation, while allowing gas exchange and maintaining sterility.

The inserts/tissue culture wells can be manufactured singly for use in for example, conventional tissue culture plates, wherein the tray 114 would be the tissue culture plate. Alternatively, the tissue culture wells/inserts can be manufactured as part of a tissue culture plate, such as for example a 24-well plate, 12 well plate, 6-well plate and the like. Cells cultured in the apparatus of the invention can be incubated in regular tissue culture incubators. The $O_2$ content of the incubator would vary depending on the optimum growth needs of the cell type.

The air useful for the present invention can be any suitable mixture of gases suitable for any cell growth including but not limited to air. In one embodiment, the volume/volume of perfluorocarbon and silicone is varied to modulate the delivery of oxygen as may be desired. Further, the culture apparatus can be incubated in varying percentages of $CO_2$, CO, NO, $O_3$, $H_2S$ or any other gas composition deemed appropriate for cell growth, viability or differentiation. For example, incubators with about 1% to 100% $O_2$, and/or hyperbaric chambers.

The lid or closing means of the tray can be of any shape or form including but not limited to a screw cap or a snap cap. The lid/closing means is dimensioned to fit the tray. Further, the closing means can be constructed from any material including but not limited to plastic. In a preferred embodiment, the closing means may contain an air filter such that the air filter does not allow the passage of microorganisms, cells, viruses or any contaminants into or out from the cell-cultivating device. Sterilizing air filters are known in the art and are commercially available, for example, from Millipore, Mass.

In another preferred embodiment, the apparatus and the cell/tissue culturing wells can be configured to the needs of the user. For example, in one embodiment, the assembly is configured in a typical tissue culture plate. Other configurations include 6-well plates, 12-well plates, 24-well plates, 96-well plates and the like. Other configurations include tissue culture flasks, containers for transporting of organs, especially those organs for use in organ transplantation, roller bottles for culturing large volumes of cells, bags and the like.

PFC Silicone Bags: PFC/Silicone mixture is injected under high pressure into a stainless steel mold (manufactured prior by CNC machining) which is the inverse of the desired object, in this case a bag. The mold comprises a solid inner portion of the bag, a thin channel for injection of the material to the desired membrane thickness and a final outer block which will serve to hold the material at the desired thickness during the curing process. The mold is generally made of two pieces, the core and the cavity, which allows for the part to be extracted after injection molding. Once the mixture has cured, it can be removed from the mold by a series of pins integrated into the mold prior to manufacture, or by air ejection through channels cut into the mold. PFC Silicone bags could be made to any desired thickness utilizing this technique.

PFC/Silicone Prototypes Compression Molding: In one example, a mold cavity was manufactured from a stainless steel block with a circular channel 8 mm deep and with a thickness of 6 mm. Air injection ports were drilled along the side of the channel to allow for mold removal. This was placed within the vise locks of a compression molder and locked flush with the main surface of the molding machine. On top of the cavity and on the surface of the compression molding machine, the PFC/Silicone mixture was poured in excess, and 300 micrometer stainless steel shims were placed along the sides of the apical molding surface (hydraulic compression surface). The top surface, which is simply a large stainless steel surface about 24"×24" was compressed down to the level of the shims and the material was allowed to cure for three hours at 37° C. At the end of the three hour period, the compressor was released, the apical surface raised and air was injected into the ports releasing a solid silicone dish with a 300 micrometer bottom membrane.

In a preferred embodiment, the apparatus comprises 96 wells and is the same size as those typically used for assays.

In another preferred embodiment, the tissue culture wells can comprise a separable insert wherein the one piece of the well comprises the membrane barrier, similar to the transwell architecture. For example, the portion of the tissue culture well used to support the growth of cells which comprises the PFC/Si membrane, is detachably secured to the portion of the device used to suspend the membrane within a well containing growth medium. This arrangement affords easy manipulation of the cultured cells.

In this configuration, the tissue culture device comprises a two-piece transwell which has two components, a cell retention element and a hanger for suspending the cell retention element within a well. The retention element is detachably secured to the bottom portion of the hanger. The cell retention element includes the PFC/Si membrane surface. The hanger is constructed and arranged such that it may be suspended from the periphery of the well, with a bottom portion of the hanger extending into the well. When the hanger is suspended from the periphery of the well, the retention element is suspended horizontally within the well.

In another preferred embodiment, the retention element comprises protruding or elevating members.

In one embodiment, the retention element is secured to the bottom of the hanger by a friction fit. In another embodiment, the retention element is secured to the bottom of the hanger by a friction fit but in an inverted orientation compared to that of the first embodiment. In yet another embodiment, the retention element is hung from the hanger.

The hanger preferably includes an outwardly extending flange which is stepped so that it may hang upon the upper end of a well in a tissue culture cluster dish. The stepped flange prevents the hanger from shifting laterally within the well, thereby keeping the side wall of the hanger spaced from the side wall of the well so as to prevent capillary action of fluid between the side wall. Capillary action is further prevented in one embodiment by the use of a funnel-shaped hanger which further removes the side wall of the hanger from the side wall of the well. The flange is discontinuous to provide an opening which allows a pipette to be inserted into the space between the hanger and the side wall of the well to provide access to the medium within the well.

The retention element preferably has a side wall defining an interior and a peripheral lip extending from the side wall. A membrane is attached to the bottom surface of the side wall forming a tissue or cell growth support. The peripheral lip permits easy manipulation of the retention element, as well as providing structure which permits the use of the retention element.

The assembly can contain one or more PFC/Si membranes and media chambers. For example, one below, one between and one above the membranes. This allows cells to be grown on the membranes for transport studies and the study of cell to cell interaction.

Still another aspect of the invention is a cluster dish having a plurality of wells containing the tissue culture device as described above.

It is an object of this invention to provide a tissue or cell culture device capable of being placed in a cluster dish such that nutrients are provided to tissues or cells while allowing access to the wells in the cluster dish for the addition or removal of media.

The three-dimensional culture system of the invention can be used in a variety of applications. These include but are not limited to cell and tissue culture, stem cell expansion and differentiation, assays, screening cytotoxic compounds, allergens, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

The cells of the present invention are preferably eukaryotic cells. In a preferred embodiment, the cells are animal cells, mammalian cells, preferably human cells. The cells can be any type of recombinant or non-recombinant eukaryotic cell, including, for example, insect cells, e.g. Sf-9; primate cells, e.g., Vero; mouse, e.g., BHK or C-127; hamster, e.g., CHO; human, e.g., tumor, transformed, non-transformed, epithelial, endothelial, osteoblasts, embryonic or mesenchymal stem cells. Any cells can be grown in the cell-cultivating device in accordance with the present invention. In particular, cells of choice for the present invention can be anchorage-dependent or anchorage-independent. Anchorage-dependent cells require a surface on which to grow whereas anchorage-independent cells can grow in liquid suspension.

In another preferred embodiment, the system/apparatus is used to culture stem/progenitor cells for the efficient differentiation of these cells. The efficient and enhanced delivery of $O_2$ to the stem cells results in enhanced differentiation levels of these cells.

In yet another embodiment, the present invention provides a cell-cultivating apparatus for growing three-dimensional tissue cultures. Culturing tissue for transplantation requires several conditions to be met before the tissue receives Food and Drug Administration (FDA) approval. Those FDA requirements, include, but are not limited to, functionality that ameliorates the disease consistency and reproducibility for growth of tissue construct; and proven sterility. To achieve in vivo functionality, engineered tissue constructs must be three-dimensional. Data from the aseptic monitoring of the growing construct can be used to validate sterility and establish specifications.

Transplantable tissue has three key features: 1) an extra cellular matrix for mechanical stability and scaffolding, 2) cell-to-cell contact to maintain viability and function and 3) a three-dimensional shape to segregate cell subpopulations for growth and proliferation. Standard tissue culture approaches (e.g.; t-flasks, petri dishes, roller bottles and stirred roller bottles) have consistently failed to yield transplantable tissue that directly supplants organ function.

Polymer formulations containing perfluorinated compounds are disclosed in U.S. Pat. No. 6,630,154 which is incorporated herein in its entirety.

Oxygen metabolism is essential for metabolic function of eukaryotic cells Particularly, with mammalian and animal cell culturing techniques, oxygen flux is important during the early stages of rapid cell division. Some mammalian and animal cells are anchorage-dependent, requiring a surface to grow, whereas other mammalian and animal cells are anchorage independent and can be grown in liquid environments regardless of the types of cells. However, these cells all require dissolved oxygen in the medium. Nevertheless, during the later phases of cell culture with both anchorage-dependent and independent cells, as the number of cells per unit volume increases, the bulk oxygen mass transfer requirements increases.

Traditionally, at least with anchorage-independent cells, increased requirements for oxygen are accommodated by mechanical stirring methods and the sparging of gases into the culture. However, both stirring and the sparging of gases can result in damaging cells, thereby decreasing the viability of the culture and the overall efficiency and productivity of the cell and/or tissue culture. Further, direct sparging of cell and tissue cultures with gas can lead to foam production, which is also detrimental to cell viability.

The present invention overcomes these deficiencies by enhanced oxygen delivery.

As an illustrative example which is not meant to limit or construe the invention in any way, the following is provided. Stainless steel forms were manufactured by BioRep, Inc. of Miami, Fla. with the following specifications: 8.5 cm inner diameter with a beveled groove along the bottom ridge about 300 microns from the bottom edge to allow for the silicone to cure in place and hold fast. These forms were fit within an outer ring, also made of stainless steel, with three feet along the outside edge, to allow for gas exchange along the bottom surface when placed in an incubator, the feet keeping the bottom surface elevated above the stainless steel shelves of the culture incubator. Another device was manufactured using Millipore CM culture inserts, removing the liquid permeable Teflon bottoms and replacing them with poured silicone/PFC. However, any geometric culture form could effectively be manufactured. The PFC/Silicone was made in the following fashion: Dow Corning RTV-615A electrical silicone was weighed (density 1.1 g/mL) to achieve a specific volume. To that, FC43 (3M corporation) was added and weighed (1.9 g/mL) such that the volume added was 10%-20% that of the silicone and catalyst to be added later at a volume percentage ratio of 10 parts silicone to 1 part catalyst. The ice-slurry cooled PFC-silicone mixture in a 50 mL conical was then sonicated using a probe sonicator at twenty second pulse intervals, starting at the bottom of the conical and gradually moving the sonicator up towards the top of the conical to homogenously disperse the PFC throughout. Five minute cooling intervals were implemented after every minute of sonication. What occurs is the formation of a white opaque mixture. The sonication continues until there is no longer evidence of phase separation between the PFC and the silicone and until the dispersion is visibly uniform. At this point, the mixture is vortexed for 1 minute to further homogenize and then is placed in a glass vacuum desiccation chamber for degassing. Degassing is done by vacuum removing air bubbles from the silicone mixture, breaking the vacuum every five to ten minutes to pop bubble. When there are no longer any visible bubble the mixture is removed from the degassing chamber and the catalyst is added by adding 10% volume to the mixture. The catalyst is much less viscous than the polymer suspension and thus, by inverting the tube carefully for several minutes, the catalyst is well dispersed throughout the silicone mixture. At this point, the open bottom areas of the forms are covered with a taut even surface of Parafilm. Then, using a plunger dispensing pipettor, which prevents adhesion of the silicone along the inside of the pipette tips, a given volume of the silicone/PFC mixture is added to the parafilm layer to obtain the desired membrane thickness. For example, in an 8.5 cm dish a membrane thickness of 300 micrometers is used, so, the volume added would be $\pi r^2 h$, or $0.03*(\pi)*(4.25)^2$ or 1.7 mL. This volume is then spread evenly across the surface by rotating the dish and allowing the silicone to spread across and entirely cover the Parafilm. Then, the dish is allowed to stand which further distributes the silicone mixture evenly as it settles along the surface. Once this is completed, the entire dish is placed in a 45° C. incubator or oven to cure overnight. Curing occurs within 6 hours, but to assure complete curing, the plates were cured for about 18 hours before utilizing the devices. Once cured, the devices can be autoclaved to insure sterility before using in cell culture, although with the smaller inserts, the plates were soaked in 70% ethanol for several hours before use.

Alternative methods of forming the cell and tissue culture apparatuses described herein may be used. For example, one method that is economical with the material usage involves individual dispensing of a precise volume of the PDMS/fluorinated silane derivative into each dish/flask frame to obtain the desired specific membrane thickness (Volume added/surface area of dish=membrane height or thickness). The combination of frame and matrix is then processed on a vibratory table, which spreads the matrix to a uniform thickness across the basal surface of the frame. The whole unit is then heat cured. This produces the end product with the membrane in place and with minimal material loss.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Perfluorinated Silicone High Oxygen Cell Culture Platforms

Culture insert bottoms were modified with a highly permeable silicone matrix impregnated with perfluorocarbon in a given volume/volume percentage. This combination provides an oxygen reservoir on the basal surface, with no barrier of medium between the cells and the air, as the bottom surface would be impermeable to liquid.

Biomedical/Electrical grade RTV silicone (RTV-615A) and the corresponding vulcanization catalyst (RTV-615B), both with a density of 1.1 g/cm$^3$, were purchased from Dow Corning Chemical. This silicone was chosen for its known biocompatibility characteristics, high oxygen solubility and high shore durometer. Since the membrane thickness greatly affects the oxygen transfer properties of the membrane, we desired the thinnest possible membrane with minimal potential for breakage.

Perfluorotributylamine (PFC), FC-43, with a density of 1.9 g/cm$^3$ was purchased from 3M corporation. Although other perfluorinated hydrocarbons have higher oxygen solubilities, FC-43 was chosen more for its chemical stability and non-reactive properties (high boiling point, low vaporization pressure), making it more amenable to mixing into the silicone.

Silicone was weighed out in a sterile 50 mL conical tube utilizing the density to obtain a given volume of silicone. For example, when 10 mL of silicone was desired, 11 g of silicone was added to the 50 mL conical (10×1.1 g/cm$^3$). To the silicone, a given fraction of FC-43 was added (10% or 20% v/v) in the same fashion. For example, to obtain a 10% v/v PFC concentration in the above 10 mL of silicone, 1.9 g of FC-43 would be added.

Due to the extreme density of perfluorocarbon compounds, they are virtually immiscible with all less dense compounds. When admixed to another component, they immediately form a two-layer system with the other substance. In order to obtain a homogenous suspension of the PFC within other liquids or less dense components, either sonication or high pressure emulsification is required. The end result of these processes is a particle suspension of perfluorocarbon micelles of micrometer to nanometer dimensions. However, with time, the micelles often begin to coalesce into larger droplets, a phenomena known as Oswaldt ripening. This is only characteristic of emulsions in non-viscous liquids, and in our previous experience with gelated polymer solutions, was not observed. The advantage of using semi-solid hydrogels or compounds such as silicone, is that they have the ability to entrap the PFC droplets within their matrices preventing or greatly reducing droplet coalescence.

The bi-layer PFC/Silicone mixtures were sonicated using a Virsonic 200 probe sonicator for 20 second pulses, with one minute cooling intervals in between, for a total sonication time of three minutes at 40 W. The mixture was continuously cooled in an ice slurry bath. The end result of sonication was a white, opaque and homogenous mixture. Once sonicated, no further phase separation of the FC-43 and the silicone was observed. At this point, a 10% v/v aliquot of the vulcanization catalyst was added to the mixture and vortexed within the suspension to obtain a homogenous distribution.

Next, the entire mixture was placed in a vacuum chamber to extract all gas bubbles from the mixture. As bubbles were drawn to the surface, the vacuum was regularly broken to cause the bubbles to burst. The entire degassing took approximately 45 minutes. The end result was a smooth, opaque suspension free of gas pockets that would otherwise affect the integrity of the silicone.

The Teflon membranes were then removed from the bottom surface of the Millipore CM inserts using sterile microsurgical forceps. Parafilm was carefully placed along the entire bottom surface. The parafilm was pulled taut over the feet of the dish and secured around the outer edge of each insert to insure a flat, rigid bottom for the silicone to cure upon.

After the Parafilm was secured, a given volume of the silicone/PFC mixture was added to the bottom surface using a special plunger pipettor designed particularly for precision pipetting of viscous liquids. Specific volumes were added to obtain precise membrane thicknesses. Utilizing the known dimensions of the inserts, a desired thickness was calculated using the formula for the volume of a cylinder, $\pi R^2 h$. It was desired to make the membranes as thin as possible and have minimal chance of membrane failure. For these reasons, a variety of membrane depths were tested. The depth of 300 µm was used to provide diffusion optimization and membrane integrity. Therefore, the volume of silicone/PFC added to each dish bottom was $\pi(0.5 \text{ cm})^2 \ast (0.03 \text{ cm})$ or 23.5 µL.

Upon the addition of the silicone/PFC mixture, the dishes were slowly rotated on a modified tube rotator to evenly distribute the solution along the entire Parafilm surface. At room temperature, the silicone curing is relatively slow, allowing for further settling of the solution once the dishes were placed upright. What was observed was that the silicone after some manual manipulation/rotation distributed further and more evenly when placed on a flat surface. Once a homogenous distribution was observed, the inserts were placed into a 40° C. oven and allowed to fully cure, which occurred within 2-3 hours.

After the silicone had completely cured, the inserts were removed from the oven and allowed to cool. Then, the Parafilm base was carefully removed, so as to not tear the silicone/PFC membrane, leaving an intact, gas permeable bottom capable of holding the liquid and tissue. Before use, the inserts were sterilized by soaking overnight in 70% ethanol followed by 30 minutes in 100% ethanol. Immediately before adding the harvested tissue, they were washed with sterile PBS five times to completely remove all of the ethanol, and then were allowed to dry on a sterile half-sheet in a laminar hood Example 2

Mathematical Modeling

Pancreatic buds were harvested and carefully measured using a graded reticule in an inverted microscope. Table 1 outlines the measurements of 18 pancreatic buds.

TABLE 1

| AVERAGE DIMENSIONS | µm width | µm length | | |
|---|---|---|---|---|
| 1 | 375 | 525 | | |
| 2 | 500 | 525 | | |
| 3 | 500 | 625 | | |
| 4 | 550 | 625 | | |
| 5 | 375 | 500 | | |
| 6 | 525 | 512.5 | | |
| 7 | 525 | 550 | | |
| 8 | 437.5 | 750 | | |
| 9 | 250 | 625 | | |
| 10 | 500 | 500 | | |
| 11 | 375 | 675 | | |
| 12 | 625 | 750 | | |
| 13 | 375 | 750 | | |
| 14 | 375 | 800 | | |
| 15 | 437.5 | 750 | | |
| 16 | 625 | 750 | | |
| 17 | 375 | 750 | | |
| 18 | 375 | 800 | | |
| average | 450.0 | 653.5 | 551.7 | |
| stdev | 99.9 | 111.8 | 105.8 | |
| cv | 22.20 | 17.11% | 19.65% | |

Mathematical modeling was performed using an ellipse with the above dimensions for all conditions assuming the third dimension was uniform along the entire bud. Oxygen consumption rate of the buds determined through the use of a stirred microliter chamber system from Instech, Inc. Briefly, three buds were placed in a chamber containing 400 µL of conventional culture medium without bicarbonate. The chamber was precalibrated to room air oxygen concentrations in medium and zero, using $NaSO_{3-}$ suspended in distilled water. At all times the temperature was maintained within the system at 37.5° C.±0.05° C. by means of a water bath titanium chamber. After the cells and medium were added to the chamber, it was sealed by means of a beveled glass cap which extruded air bubbles and excess medium through a side port and brought the final volume to 250 µL. The spectroscopic software monitored and recorded oxygen partial pressure every second throughout the duration of measurement. Oxygen profiles were analyzed from partial pressures below 140 mmHg, when the system had stabilized thermally, to a point of adequate linearity, usually around 70-80 mmHg.

The slope was converted from mmHg to µM through the use of a conversion factor (210/158.8). Next, the converted slope in µM was converted to micromols of oxygen consumed by multiplying by the chamber volume. This value was divided by 60 to convert per minute consumption to per second consumption, and then finally, the whole amount was divided by the volume of all the buds utilized, in $m^3$ of tissue, to get a final consumption rate in $mol/m^3 \cdot s^{-1}$. This was performed on every individual batch of buds that were harvested and what was observed was that the consumption rate was very consistent irrespective of the harvest. Table 2 shows the individual consumption rates and the average utilized in the mathematical modeling.

TABLE 2

| BUD OCRs | Mol/m3 s |
|---|---|
| experiment 2 | OCR |
| 1 | 8.35E−03 |
| 2 | 9.68E−03 |
| experiment 3 | |
| 1 | 8.57E−03 |
| 2 | 7.97E−03 |
| experiment 4 | |
| 1 | 9.53E−03 |
| mean | 8.82E−03 |
| stdev | 7.49E−04 |
| cv | 8.50% |

Culture conditions were modeled using Comsol Multiphysics 3.2 Finite Element Modeling software. Conventional culture conditions were modeled with the following parameters. Initial oxygen concentration was assumed to be 0.1995 $mol/m^3$ based on conventional 95% RA/5% $CO_2$ culture conditions. The diffusivity of oxygen through the medium was taken to be that of oxygen through water at 37° C., 3.3 E-09 $m^2/s$. The diffusivity of oxygen through the tissue was also taken from the average of values reported in the literature, 1.3 E-09 $m^2/s$. The oxygen consumption rate was assumed to be first order with a Km value of 5.81 E-04 $mol/m^3$, also based on literature values for endocrine oxygen consumption and was modeled as $Rm \ast (c/(c+Km))$, based on Michaelis-Menten kinetics. The Rm value utilized was the average value shown above in the table of 8.82 E-03 $mol/m^3$ of tissue. The boundary conditions utilized were initial concentration along the top surface of the culture medium of a height of 2.65 mm and 3.15 mm in the PFC silicone dishes, and either oxygen concentration with a diffusion coefficient in medium on the bottom surface of the dish, or enhanced oxygen effective diffusion in the case of the pfc/silicone dishes. Culture was modeled with two and three buds in a dish, clustered together, as was observed, and kept separated. Oxygen profiles were determined across the dimensional distances for each bud. Anoxic tissue percentage was calculated as tissue where the oxygen concentration at equilibrium was less than the Km value, 5.81 E-04 mol/m$^3$ of the oxygen consumption rate, again taken from literature assumptions. Table 3 summarizes the anoxic tissue calculations for all culture conditions, assuming either two buds or three buds per 1 cm dish.

TABLE 3

| CULTURE CONDITIONS | ANOXIC % | $O_2$ minimum |
|---|---|---|
| 2 buds apposing conventional | 59% | |
| 2 buds apposing high oxygen | 30% | |
| 2 buds apposing pfc silicone | 0% | 0.083 |
| 2 buds separated conventional | 33% | |
| 2 buds separated high oxygen | 11% | |
| 2 buds separated pfc silicone | 0% | 0.134 |
| 3 buds apposing conventional | 68% | |
| 3 buds apposing high oxygen | 41% | |
| 3 buds apposing pfc silicone | 0% | 0.038 |
| 3 buds separated conventional | 43% | |
| 3 buds separated high oxygen | 24% | |
| 3 buds separated pfc silicone | 0% | 0.12 |

Additional modeling demonstrated that the PFC Silicone also has an advantage when compared with culture platforms comprised solely of silicone. In the case of the pancreatic buds, the average difference in oxygen concentration was a 0.012 mol/m$^3$ increase in localized oxygen concentration in the PFC/Silicone plates compared to the Silicone, alone. This is extremely important as we have observed that even small differences in oxygen concentration can drastically affect the relative fold increase of endocrine marker gene expression during culture of the embryonic tissue. Based on this modeling information, experiments were undertaken to assess the effects on differentiation of increased oxygen. The experimental design and results are detailed in the next example.

Example 3

Oxygen Transfer Studies

The purpose of these studies was to assess the representative oxygen transfer characteristics of the PFC/Silicone systems relative to silicone alone and conventional plastic culture systems, where oxygen comes primarily from the apical surface.

Use of Optical Oxygen Sensors Based on Fluorescence Decay to Measure Oxygen Transfer:

Materials: 2.4 cm PFC Silicone, Silicone and plastic dishes.

Thin film optical spot oxygen sensors (PreSens Inc, Germany and WPI Inc, Sarasota, Fla.) were utilized for measurement of oxygen concentration. These sensors are approximately 5 mm in diameter and 50 µm thick. These sensors are generally fastened inside of a culture system on a flat surface and a fiber optic detection cable is fastened non-invasively to the outside of the culture platform, fluorescence values (intensity and phase angle) to a detector and software package for analysis. The sensors are based on fluorescence decay over time (life-time fluorescence) and are constructed of oxygen sensitive fluorophores with fluorescence characteristics inversely proportional to the amount of oxygen present. The sensors are incredibly stable and once calibrated can be reused multiple times and autoclaved, as needed. Drift is minimal and can easily be countered by a spot calibration at a known temperature and room air partial pressure. The picture below details the sensor/fiber assembly for measurement: Spot sensors were fastened to the bottom center region of PFC/Silicone (10% v/v FC-70, FC-43), silicone and plastic (polystyrene) 2.4 cm inserts with rapid curing silicone. SMA connectors were glued on the outside bottom of the 6 well plates aligned such that the sensor fluorescent surface was flush with the optical outlet of the SMA connector.

After the glue had cured, the fiberoptic transmission cables were secured in the SMA connectors and the signal transmission was tested to insure that the fluorescent signal could pass through the silicone, PFC/Silicone and plastic with adequate intensity to be analyzed. The separation distance of several millimeters between the fiber optic probe and the spot sensors generated no artefactual readings or signal intensity issues.

The well plate was then placed into a 37° C. standard 5% $CO_2$ incubator and 1.8 mL of dd$H_2O$ was added to each dish. Then, the well plate was covered and the system was allowed to equilibrate while monitored for approximately 1 hour. When the system had reached equilibrium and was reading close to the expected oxygen partial pressure of 142 mmHg, the software recording was started for a 10 minute baseline reading. At the end of the 10 minute baseline read, 18 µL of a freshly made and pre-warmed 1M sodium sulfite solution was added to each well by initial pipetting and then a thorough mixing by further pipetting.

The sodium sulfite is a well-established and utilized system for oxygen removal. At equilibrium, water will contain approximately 192 µM dissolved oxygen which is far less than the 10 mM final concentration of sodium sulfite upon addition of the 1M stock. Thus, there is a rapid and extreme consumption of oxygen that far exceeds any cell type in culture and therefore, it can be used as a "worst case scenario" control for any system. The volume of water (1.8 mL) chosen for use was to insure a sufficient medium height (4 mm) such that most of the oxygen transfer measured by the sensor in the membrane systems would be due to diffusion through the membrane as the gradients from the apical to the basal surface would be large and would take some time to equilibrate ($L^2$/D; where L is the path length of diffusion from the surface to the sensor in centimeters and D is the diffusivity of oxygen in water at 37° C., 3.0 E-05 cm$^2$/s). Oxygen values were recorded until the systems returned to at least 95% of the baseline value. Oxygen transfer comparisons were made using the slope during return to baseline $O_2$ and the time to half maximal oxygen concentration T at: (maximal concentration-minimal concentration)/2. These studies were performed after the curing period of 24 hours post-manufacture, to minimize loss due to PFC volatility.

Figure 3:
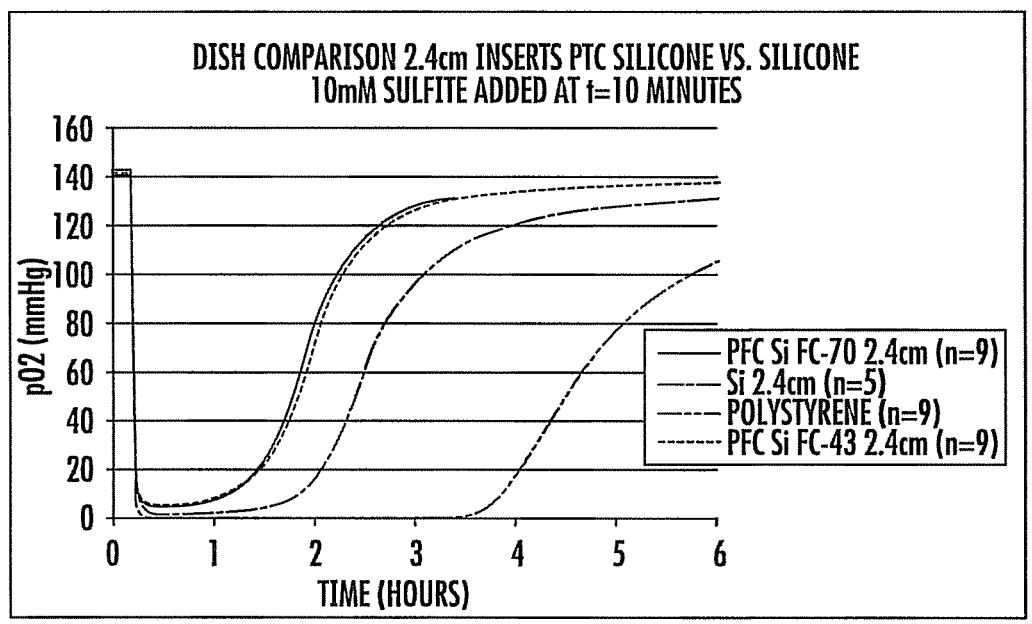
FIG. 3 is a graph showing the results of the comparison of all dish types at 24 hours post manufacture. The figure shows representative average curves of replicate runs of each group. No error bars are displayed, but the differences between the PFC/Silicone platforms vs. the silicone alone and vs. the polystyrene were highly significant in favor of the PFC/Silicone platforms ($P<0.01$ vs. the silicone alone and the polystyrene for time to half maximal concentration and rate of reoxygenation slope).
Figure 4:
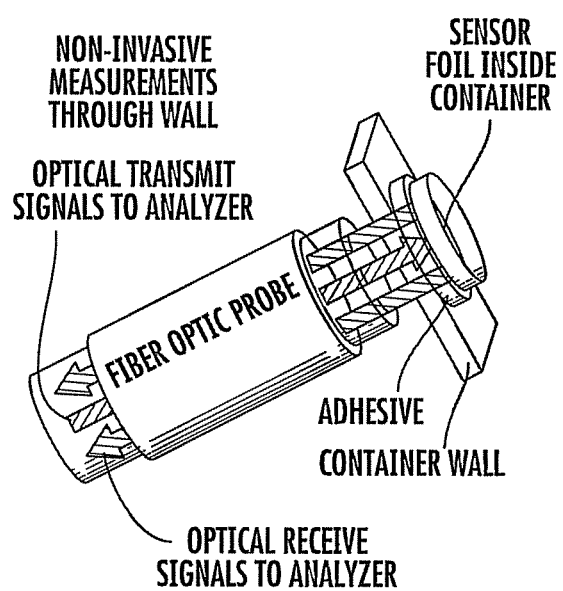
FIG. 4 is a schematic representation of a thin film optical spot oxygen sensor.

Results:

FIG. 3 details the results of the comparison of all dish types at 24 hours post manufacture. The figure shows representative average curves of replicate runs of each group. No error bars are displayed, but the differences between the PFC/Silicone platforms vs. the silicone alone and vs. the polystyrene were highly significant in favor of the PFC/Silicone platforms (P<0.01 vs. the silicone alone and the polystyrene for time to half maximal concentration and rate of reoxygenation slope). The differences between the FC-70 platforms vs. the FC-43 platforms were not statistically significant, although there was a trend that favored the FC-70 relative to the FC-43 for both rate of reoxygenation and time to half maximal concentration. Clearly, the PFC/Silicone platforms offer a substantial improvement over both the plain silicone and the polystyrene dishes in terms of oxygen transfer capabilities.

Currently, experiments are ongoing to study the transfer rates over time in conjunction with the observed loss of PFC due to volatility. Additionally, experiments will be performed using lower media heights to better simulate cell culture and mathematical models are being generated to describe the culture observations and for use in further system optimization.

Example 4

Optimization of Manufacturing Process

Important to the development of PFC/Silicone culture platforms is the ability to manufacture individual batches of dishes with minimal variation. Each manufacturing variable was carefully examined to develop an optimal method for generating reproducibly homogeneous micellar suspensions of the perfluorocarbon within the silicone and catalyst mixture insuring uniform perfluorocarbon concentrations throughout the membrane matrix prior to the curing process.

Methods.

PFC/Silicone Manufacture:

After manipulation of component variables and processing settings, as well as studies of the stability of the PFC to determine volatility properties and optimal transfer characteristics, an optimal manufacturing protocol was formulated. The steps detail the protocol. In this example, 10 mL of the 10% v/v PFC, 20% catalyst membrane composition is manufactured and 2.4 cm transwell inserts are generated from the PFC/Silicone solution.

Materials:

RTV615-A GE Silicone, RTV615-B catalyst for RTV615-A, and 3M Inc. FC-70 Fluorinert liquid.

Pour an excess of silicone into a 50 mL conical tube. Centrifuge silicone for 5 minutes at approximately 1000 g with a counterbalance tube filled with water. This is to de-gas the silicone. Weigh a 50 mL conical tube (w/o the) cap in a conical tube holder and record the weight. Careful not to introduce air bubbles into the silicone, pipette 7 mL of the silicone into the weighed 50 mL conical tube. It is necessary to use a plunger pipettor common for the transfer of viscous solutions as a conventional pipettor will not extrude an accurate volume as most of the silicone will stick to the pipette tip walls. To insure that 7 mL of the solution have been added to the tube, weigh the tube again and subtract the initial weight. This will give the weight of the silicone alone. Divide this number by the density of the silicone and this will give the volume of silicone added. For example, the density of the silicone is 1.013 g/mL and therefore, 7 mL should produce a weight of 7.091 g. Prepare an ice slurry in a bucket by mixing ½ the bucket of ice with ½ cold water. In a hood, place the 50 mL conical containing the silicone held with a ring stand and clamp such that the entire volume of silicone is immersed in the ice slurry. Place 3/16" sonicator probe tip (VirTis 390910 for Virsonic 100) held onto ring stand with another clamp into the silicone place the tip ⅛" from the conical tube bottom. Care must be taken to insure that the sonicator tip does not touch any part of the conical tube and remains centered in the bottom. Start sonicating the solution at 25-30 W (setting 16 on the VirSonic 100 sonicator). The silicone will make the sonicator sound as if it is not tuned, but proceed by adding 1 mL of the FC-70 with a plunger pipettor. Try to get the pipette tip as close to the probe as possible. This will insure that the PFC begins mixing upon introduction into the silicone. As the PFC in much denser than the silicone (p=1.9243 g/mL), it will sink rapidly to the bottom of the tube. Stop sonicating after 30 seconds and allow the solution to cool in the ice bath for 30 seconds. Repeat this step two additional times for a total of 3 sonications. After the $3^{rd}$ sonication, do not allow the sample to cool for 30 seconds. Instead of allowing the solution to cool for the last 30 seconds, raise the probe tip from the solution, which should now begin to look whitish and opaque, allow the excess to drip back into the conical and then, remove the conical tube from the clamp placing cap onto conical. Vortex the solution for 1 minute on highest setting. Return mixture to ice slurry, remove cap and place sonicator probe tip back in prior position in mixture. If ice slurry is warming and ice is disappearing at any step, replace slurry with amounts described above. Let solution cool for 1 minute. Sonicate the solution as above, 30 seconds pulse on and 30 seconds cooling, for an additional 3 times (Now 6 cycles total). Raise the probe tip, allow excess to drip back into mixture and then remove mixture from clamp and slurry. Place cap back onto tube and fasten tightly. Centrifuge at 1000 g for 5 minutes with balance tube in place (this is to remove air bubbles and assess if any PFC is not mixed). Remove mixture from centrifuge, remove cap from conical tube and add 2 mL of catalyst solution to the mixture. Stir in catalyst thoroughly with a sterile spatula. Remove spatula from mixture scraping off excess solution into tube. Replace tube cap and fasten tightly. Vortex solution for 1 minute, as above. Centrifuge solution final time, as above.

The general outcome of this processing is a homogeneous, opaque and viscous micellar suspension. These protocols produce a suspension free of phase separation. Often, there is a very thin and more transparent layer near the top of the mixture that is likely due to the inability of the sonicator to force the mixing entirely to the top. For this reason we generally take aliquots for the platform manufacture from the central region of the mixture (in the vertical direction) as we observe the most reproducible uniformity in this portion. The next experiments will use flow through sonicators that will continuously mix the volumes together during processing.

Dish Manufacture:

Corning 2.4 cm transwell permeable supports (for 6-well plate), Parafilm, Scalpel for membrane removal.

Remove desired number of transwell inserts from sterile packaging. Using scalpel, carefully cut through polycarbonate membrane bottom and peel membrane completely away from insert plastic frame. Place a square of parafilm large enough to cover bottom of insert and pull taut along insert frame careful to not wrinkle parafilm. This will serve as a temporary platform on which the PFC/Silicone will cure. The volume added to each dish is determined by the desired membrane thickness calculated using the following formula:

$$V = \pi r_m^2 T_d \qquad (1)$$

where V is the volume added, r is the radius of the culture platform and $T_d$ is the desired membrane thickness. The typical membrane thickness we utilize to insure even distribution across the platform surface with minimal variation is 650 μm, although using other fabrication methods (compression molding) we are able to generate more uniform and thinner membranes. With a membrane thickness of 650 μm, the needed volume of the PFC/Silicone mixture is 295 μL. If using the plates for volatility studies or homogeneity determinations, see instructions below, otherwise carefully pipette, using the plunger pipettor, 295 μL of the PFC/Silicone composition into the center of each dish. Care should be taken to prevent introduction of air bubbles into the mixture and to insure that the pipette tip is completely filled when the mixture is aspirated. When ejecting the volume, take care to make sure all the mixture is extruded removing the last droplet by touching the pipette tip to the parafilm surface. The mixture will spread evenly across the parafilm surface with time, but if regions of the parafilm remain uncovered, hold the dish at 90° with the uncovered region in a basal orientation so that the mixture will flow downward and coat the parafilm. Rotate the dish as needed to insure even coating. Place the dishes in 6 well plates and cover with plate lid. Put into 37° C. incubator to cure overnight. After overnight period, touch a pipette tip to the surface of several dish membrane surfaces to see that the curing has reached completion (should be flexible and resilient, not sticky or tacky). Peel the parafilm carefully off of each dish bottom. The membrane may stretch as the parafilm is pulled away, but they should separate with no tearing or breakage. At this point the dishes are ready for use.

Homogeneity Determination:

For each batch of dishes manufactured, gravimetric measurements were utilized to determine the volume percentage of PFC in each individual dish manufactured relative to the ideal calculated from the known volume additions of each component of the matrix. As an example, the following details the manufacture of dishes comprised of 10% v/v PFC (FC-70), 20% v/v catalyst and 70% v/v silicone: An initial volume of PFC/Silicone is manufactured as above. Assuming a 110 mL initial volume of membrane material, the ideal weight of the mixture in any individual dish would be equal to $$V_{mixture(ml)} \times (0.7 \times \rho_{silicone} + 0.2 \times \rho_{catalyst} + 0.1 \times \rho_{PFC}) \quad (2)$$

In a dish containing 295 µL of the aforementioned 10% mixture (2.4 cm D circular culture insert), the ideal weight would be: 0.295×(0.7×1.0132+0.2×0.9918+0.1×1.9243) or, 0.3245 g. As each dish is manufactured, the weight of each individual dish/parafilm frame is recorded and then the weight of each dish/parafilm frame with the 295 µL PFC/Silicone is recorded. From this weight, relative to the ideal weight, the volume of PFC in each dish is calculated. Averages, standard deviations and coefficients of variation are tabulated for each batch.

Results:

Early batch production and mixture manufacture resulted in more variable volume percentage incorporations. Important variables such as temperature, sonication power, sonication time and sonication repetitions were found to be most important in reproducibility. Pipetting technique in applying the mixture to the frame was also found to be very important. The early batches had coefficients of variation ranging from 7-15%, but the above manufacturing protocol has resulted in far better reproducibility with coefficients of variation <1%.

Tables 8-10, detail the measurements taken in a batch of 13.82% v/v PFC, 10% v/v PFC and 5% v/v PFC dishes after manufacture.

TABLE 8

13.82% v/v PFC Culture Platforms

| Dish | Time 0 wt dish + parafilm | dish + parafilm + PFCSi | 295 uL PFC Si PFC Si alone | p PFC Ai alone | volume PFC per 295 uL | wc PFC per 295 uL | volume % PFC |
|---|---|---|---|---|---|---|---|
| 13.82% IDEAL (perfectly homogenous) | | | 0.335 | 1.1356 | 40.77 | 0.0785 | 13.82% |
| A1 | 2.5699 | 2.9029 | 0.333 | 1.12881 | 40.53 | 0.078 | 13.74% |
| A2 | 2.5837 | 2.922 | 0.3383 | 1.14678 | 41.17 | 0.0792 | 13.96% |
| A3 | 2.5725 | 2.9099 | 0.3374 | 1.14373 | 41.06 | 0.079 | 13.92% |
| A4 | 2.5661 | 2.9042 | 0.3381 | 1.1461 | 41.15 | 0.0792 | 13.95% |
| A5 | 2.5555 | 2.8892 | 0.3337 | 1.13119 | 40.61 | 0.0781 | 13.77% |
| A6 | 2.5628 | 2.9019 | 0.3391 | 1.14949 | 41.27 | 0.0794 | 13.99% |
| B1 | 2.5665 | 2.9043 | 0.3378 | 1.1451 | 41.11 | 0.0791 | 13.94% |
| B2 | 2.5348 | 2.8736 | 0.3388 | 1.1485 | 41.23 | 0.0793 | 13.98% |
| B3 | 2.5531 | 2.887 | 0.3339 | 1.319 | 40.64 | 0.0782 | 13.77% |
| B4 | 2.5781 | 2.9093 | 0.3312 | 1.227 | 40.31 | 0.0776 | 13.66% |
| B5 | 2.5782 | 2.912 | 0.3338 | 1.315 | 40.62 | 0.0782 | 13.77% |
| B6 | 2.5584 | 2.8947 | 0.3363 | 1.14 | 40.93 | 0.0788 | 13.87% |
| MEAN | | | | | 40.89 | 0.0787 | 13.86% |
| SD | | | | | 0.33 | 0.0006 | 0.11% |
| CV | | | | | 1% | 1% | 0.80% |

TABLE 9

10% v/v PFC Culture Platforms
10% v/v PFC Culture Platforms

| Dish | Time 0 wt dish + parafilm | dish + parafilm + PFCSi | 295 uL PFC Si PFC Si alone | p PFC Ai alone | volume PFC per 295 uL | wc PFC per 295 uL | volume % PFC |
|---|---|---|---|---|---|---|---|
| 10% IDEAL (perfectly homogenous) | | | 0.03245 | 1.09989 | 29.5 | 0.0568 | 10.00% |
| A1 | 2.5549 | 2.8749 | 0.3200 | 1.08475 | 29.1 | 0.0560 | 9.86% |
| A2 | 2.5748 | 2.8977 | 0.3229 | 1.09458 | 29.4 | 0.0565 | 9.95% |

TABLE 9-continued

10% v/v PFC Culture Platforms
10% v/v PFC Culture Platforms

| Dish | Time 0 | | 295 uL PFC Si | | volume | wc PFC | volume % |
|---|---|---|---|---|---|---|---|
| | wt dish + parafilm | dish + parafilm + PFCSi | PFC Si alone | p PFC Ai alone | PFC per 295 uL | per 295 uL | PFC |
| A3 | 2.5497 | 2.8734 | 0.3237 | 1.09729 | 29.4 | 0.0566 | 9.98% |
| A4 | 2.558 | 2.8818 | 0.3238 | 1.09763 | 29.4 | 0.0566 | 9.98% |
| A5 | 2.5994 | 2.9233 | 0.3239 | 1.09797 | 29.4 | 0.0567 | 9.98% |
| A6 | 2.5533 | 2.8786 | 0.3253 | 1.10271 | 29.6 | 0.0569 | 10.02% |
| B1 | 2.5638 | 2.8874 | 0.3236 | 1.09696 | 29.4 | 0.0566 | 9.97% |
| B2 | 2.5521 | 2.8763 | 0.3242 | 1.09898 | 29.5 | 0.0567 | 9.99% |
| B3 | 2.5745 | 2.8983 | 0.3238 | 1.09763 | 29.4 | 0.0566 | 9.98% |
| B4 | 2.565 | 2.8885 | 0.3235 | 1.09661 | 29.4 | 0.0566 | 9.97% |
| B5 | 2.5649 | 2.8907 | 0.3258 | 1.10441 | 29.6 | 0.0570 | 10.04% |
| B6 | 2.567 | 2.8911 | 0.3241 | 1.09864 | 29.5 | 0.0567 | 9.99% |
| C1 | 2.5336 | 2.8589 | 0.3253 | 1.10271 | 29.6 | 0.0569 | 10.02% |
| C2 | 2.5447 | 2.8681 | 0.3234 | 1.09627 | 29.4 | 0.0566 | 9.97% |
| C3 | 2.5277 | 2.8520 | 0.3243 | 1.09932 | 29.5 | 0.0567 | 9.99% |
| C4 | 2.5451 | 2.8699 | 0.3248 | 1.10102 | 29.5 | 0.0568 | 10.01% |
| C5 | 2.5421 | 2.8660 | 0.3239 | 1.09797 | 29.4 | 0.0567 | 9.98% |
| C6 | 2.5721 | 2.8943 | 0.3222 | 1.09220 | 29.3 | 0.0564 | 9.93% |
| D1 | 2.5207 | 2.8445 | 0.3238 | 1.09763 | 29.4 | 0.0566 | 9.98% |
| D2 | 2.5675 | 2.8926 | 0.3251 | 1.10203 | 29.6 | 0.0569 | 10.02% |
| D3 | 2.5729 | 2.8968 | 0.3239 | 1.09797 | 29.4 | 0.0567 | 9.98% |
| D4 | 2.547 | 2.8713 | 0.3243 | 1.09932 | 29.5 | 0.0567 | 9.99% |
| D5 | 2.5514 | 2.8757 | 0.3243 | 1.09932 | 29.5 | 0.0567 | 9.99% |
| D6 | 2.5406 | 2.8653 | 0.3247 | 1.10068 | 29.5 | 0.0568 | 10.01% |
| MEAN | | | 0.3239 | | 29.45 | 0.0567 | 9.98% |
| SD | | | 0.0012 | | 0.1050 | 0.0002 | 0.04% |
| CV | | | 0.36% | | 0.36% | 0.36% | 0.36% |

TABLE 10

5% v/v PFC Culture Platforms

| 5% | Time 0 | | 295 uL PFC Si | | volume | wc PFC | volume % |
|---|---|---|---|---|---|---|---|
| | wt dish + parafilm | dish + parafilm + PFCSi | PFC Si alone | p PFC Ai alone | PFC per 295 uL | per 295 uL | PFC |
| IDEAL (perfectly homogenous) | | | 0.312 | 1.056 | 14.86 | 0.0286 | 5.04% |
| C1 | 2.5631 | 2.8668 | 0.3037 | 1.029491525 | 14.49 | 0.0279 | 4.91% |
| C2 | 2.5855 | 2.8927 | 0.3072 | 1.041355932 | 14.65 | 0.0282 | 4.97% |
| C3 | 2.61 | 2.9222 | 0.3122 | 1.058305085 | 14.89 | 0.0287 | 5.05% |
| C4 | 2.5636 | 2.874 | 0.3104 | 1.05220339 | 14.80 | 0.0285 | 5.02% |
| C5 | 2.5472 | 2.8567 | 0.3095 | 1.049152542 | 14.76 | 0.0284 | 5.00% |
| C6 | 2.5524 | 2.8631 | 0.3107 | 1.053220339 | 14.82 | 0.0285 | 5.02% |
| D1 | 2.5702 | 2.882 | 0.3118 | 1.056949153 | 14.87 | 0.0286 | 5.04% |
| D2 | 2.5524 | 2.863 | 0.3106 | 1.052881356 | 14.81 | 0.0285 | 5.02% |
| D3 | 2.5462 | 2.8581 | 0.3119 | 1.057288136 | 14.88 | 0.0286 | 5.04% |
| D4 | 2.5559 | 2.8682 | 0.3123 | 1.058644068 | 14.90 | 0.0287 | 5.05% |
| D5 | 2.5524 | 2.8644 | 0.312 | 1.057627119 | 14.88 | 0.0286 | 5.04% |
| D6 | 2.5696 | 2.8815 | 0.3119 | 1.057288136 | 14.88 | 0.0286 | 5.04% |
| E2 | 2.5486 | 2.8606 | 0.312 | 1.057627119 | 14.88 | 0.0286 | 5.04% |
| E3 | 2.5594 | 2.8713 | 0.3119 | 1.057288136 | 14.88 | 0.0286 | 5.04% |
| E4 | 2.5693 | 2.88 | 0.3107 | 1.053220339 | 14.82 | 0.0285 | 5.02% |
| E5 | 2.5639 | 2.875 | 0.3111 | 1.054576271 | 14.84 | 0.0286 | 5.03% |
| MEAN | | | | | 14.82 | 0.03 | 5.022% |
| SD | | | | | 0.11 | 0.0002 | 0.0365% |
| CV | | | | | 0.727% | 0.727% | 0.727% |

Discussion:

The above batches platforms exhibit the low variation observed utilizing the current manufacturing protocol regardless of the v/v % of perfluorocarbon added to the matrix. Clearly, this data demonstrates that manufacture of this material lends itself to mass production protocols and can be readily scaled up with automated system.

Example 5

PFC Volatility Studies—Determining Optimal Perfluorocarbon

The most important component of the culture platforms as related to the enhancement of oxygen transfer is the perfluorocarbon utilized. Perfluorocarbons are extremely dense and chemically inert liquids that have a high solubility for oxygen and additionally, have oxygen transfer characteristics similar, often superior to hemoglobin (linear vs. signoidal bind/release curves). However, perfluorocarbons are also typically volatile, vaporizing at standard temperatures and pressures. The rate of vaporization is dependent on the boiling point and vapor pressure of the individual PFCs and additionally, the temperature. Vapor pressure is an indication of a liquid's evaporation rate. It relates to the tendency of molecules and atoms to escape from a liquid or a solid. A substance with a high vapor pressure at normal temperatures is often referred to as volatile. The higher the vapor pressure of a material at a given temperature, the lower the boiling point.

The vapor pressure of any substance increases non-linearly with temperature according to the Clausius-Clapeyron relation:

$$\frac{dP}{dT} = \frac{L}{T\Delta V} \quad (1)$$

where P is pressure, T is temperature, L is the latent heat of the substance and $\Delta V$ is the volume change of the phase transition from liquid to gas. As temperature increases, the vapor pressure also increases and thus, the volatility also increases. We tested a clinical grade PFC, perfluorodecalin, and two perfluorocarbons used in artificial blood emulsions, FC-43 and FC-70, characterized by low vapor pressures and high boiling points.

Determination of PFC Volatility: Effect of Temperature, Boiling Point and Vapor Pressure:

Materials: Perfluorodecalin, FC-43, FC-70 Fluorinert liquid and 35 mm petri dishes.

For these studies, a 35 mm petri dish was marked and weighed empty with the lid. Next, 1 mL of PFC was added to each dish for every PFC above in quadruplicate and weighed with the lid. The initial weights of the dish and dish+PFC were recorded. The difference was recorded as the T0 PFC weight. As 1 mL was used for all measurements, % volume losses were later determined by the following formula:

$$\Delta\% V = (\Delta\text{weight}/T_0\text{weight}) \times 1 \text{ Ml} \quad (2)$$

The dishes were then stored overnight in various temperatures (50° C., 37° C. and 25° C.).

Of the three perfluorocarbons tested, perfluorodecalin has the lowest boiling point and the highest vapor pressure and therefore, it was expected that it would have the highest rate of vaporization. After 24 hours, all of the perfluorodecalin had evaporated in the 50° C. and 37° C. conditions with approximately 5% volume remaining at room temperature. As expected from the perfluorocarbon properties, the FC-70 with a higher boiling point (215° C. vs. 174° C.) and a lower vapor pressure (0.1125 mmHg vs. 1.44 mmHg) had the least volume % loss while FC-43 was slightly higher in some conditions (50° C.: 0.9% per hour vs. 0.80% per hour) and markedly higher in others (37° C. and 25° C. 0.2% vs. 0.05% at 37° C. and 0.1% vs. 0.01% at 25° C.). As expected, loss was directly related to temperature, with greater losses occurring at higher temperatures, and was also related to humidity, as dishes in humidified incubators experienced less loss than those in the curing oven (37° C.). The FC-70 was the optimal PFC with regards to volatility. FC-70, was more stable, more chemically inert, had similar material safety data, and additionally, had higher oxygen solubility and transfer characteristics.

Volatility of PFC in PFC/Silicone Matrix Culture Platforms:

These studies were performed to assess the stability of the FC-70 within the silicone matrix during curing and storage, the effect of loss on oxygen transfer and to develop means of long-term storage to minimize PFC loss. In these studies, dishes of varying volume percentage FC-70 were manufactured (5%, 13.86% and 10%). For each batch of dishes manufactured, gravimetric measurements were utilized to determine the volume percentage of PFC in each individual dish manufactured relative to the ideal calculated from the known volume additions of each component of the matrix.

As an example, the following details the manufacture of dishes comprised of 10% v/v PFC (FC-70), 20% v/v catalyst and 70% v/v silicone: An initial volume of PFC/Silicone is manufactured as above. Assuming a 10 mL initial volume of membrane material, the ideal weight of the mixture in any individual dish would be equal to $$V_{mixture(mL)} \times (0.7 \times \rho_{catalyst} + 0.2 \times \rho_{catalyst} + 0.1 \times \rho_{PFC}) \quad (2)$$

In a dish containing 295 μL of the aforementioned 10% mixture (2.4 cm D circular culture insert), the ideal weight would be: 0.295×(0.7×1.0132+0.2×0.9918+0.1×1.9243) or, 0.3245 g. As each dish is manufactured, the weight of each individual dish/parafilm frame is recorded and then the weight of each dish/parafilm frame with the 295 μL PFC/Silicone is recorded. From this weight, relative to the ideal weight, the volume of PFC in each dish is calculated. Averages, standard deviations and coefficients of variation are tabulated for each batch.

The dishes were broken into equal n based on the total number manufactured and stored in various conditions after initial curing at 37° C. (25° C., −20° C., 25° C. with 2 mL 70% ethanol and 25° C. with 2 mL culture medium). These studies were different from earlier PFC volatility studies in that there were now two surfaces (both sides of membrane exposed to air or to medium, not plastic) and thus, twice the surface area from which FC-70 could evaporate. The dish weights were taken every 24 hours and recorded and from the Δ weight, the percent loss of PFC could be tabulated, as earlier control studies with silicone alone demonstrated that all observed weight loss during curing was due to PFC vaporization and no changes in weight were observed in silicone/catalyst dishes manufactured the same way.

Results:

In all groups, there was gradual loss of PFC in all dishes that followed a non-linear pattern of volatility as dictated by the characteristics of vapor pressure equilibrium. The rate of loss was dependent on initial v/v % concentration (higher concentration, higher rate of loss), temperature (higher temperature, higher rate of loss), humidity (non-humidified, greater loss) and environmental exposure volume (open air vs. covered plate, open air greater loss). The dishes stored at −20° C. had the lowest rate of loss but those stored at 25° C. with 2 mL of 70% ethanol in a covered plate had non-statistically significant differences in loss rate. Utilization of ethanol as a storage medium does not lend itself to packing or shipment, however, but it is the preferred means of sterilization of the platforms before use in culture in our laboratory.

Discussion:

Utilizing rates of loss and the limit of PFC mixture into the silicone (approximately 20% v/v), theoretical calculations show that total PFC loss could occur in the order of 54 days. This means that different storage means will have to be developed or else dishes will have to be utilized as short-term disposable products. Oxygen transfer experiments, however, demonstrated that the oxygen transfer capabilities were not greatly affected by loss over time in the short-term, in fact getting better. On-going experiments are being conducted to determine the effect of other means of storage in sealed packages with less exposure to environmental air, thus, reducing equilibration induced evaporation. Further experiments are being conducted to assess loss in humidified culture environment and the effects of this loss on longer term oxygen transfer (>7 days).

Example 6

Enhanced Oxygenation Promotes Beta Cell Differentiation In Vitro

We tested the hypothesis that a more physiological mode of $O_2$ delivery system, would result in enhanced rates of endocrine differentiation. We observed a very significant up-regulation of all tested pancreatic differentiation genes in the experimental group compared to controls cultured in standard conditions. Endocrine-to-exocrine and β-to-α cell differentiation ratios were also significantly higher, not only compared to in vitro controls but also to the corresponding in vivo stage of development. While high $O_2$ enhanced the proliferation of epithelial cell types both in standard and PFC/Si platforms, the positive effect on endocrine differentiation was seen only in the latter. Potential molecular mechanisms underlying these effects are discussed in the context of the definition of strategies to improve the yield and functionality of β cells from stem and/or progenitor cells in vitro.

Materials and Methods

Manufacture of PFC/Si Dishes:

Biomedical/Electrical grade RTV silicone (RTV-615A) and the corresponding vulcanization catalyst (RTV-615B), both with a density of 1.1 g/cm$^3$, were utilized for the manufacture of silicone membranes (Dow Chemical, Co., Marietta, Ga.). Perfluorotributylamine, FC-43, with a density of 1.9 g/cm$^3$ was used as the perfluorocarbon oxygen moiety in the membranes (3M Inc., St. Paul, Minn.). 20% PFC/Silicone mixtures were sonicated for 3 minutes at 20 W and then placed in a vacuum chamber (45 minutes) to extract gas bubbles. Teflon membranes were removed from Millipore CM inserts, and Parafilm™ (Sigma-Aldrich Inc., St-Louis, Mo.) carefully placed along the entire bottom surface to provide a flat, rigid bottom for the silicone to cure upon. 35 μl of the mix were added to each insert and cured at 40° C. for 2-3 h. The final thickness of the membranes, once the parafilm was peeled out, was 450 μm, which was found to be the best compromise between diffusion optimization and membrane integrity.

Real-Time PCR Assays:

The assays used were: PCNA (Mm00448100_g1) Carboxypeptidase A (Mm00465942_m1); Amylase (Mm02342487_g1); Insulin 1 (Mm01259683_g1); Insulin 2 (Mm00731595_gH); Glucagon (Mm00801712_m1); Ptf1a (p48) (Mm00479622_m1); Pdx1 (Mm00435565_m1); Isl-1 (Mm00627860_m1); Ngn3 (Mm00437606_s1); Pax4 (Mm01159035_g1); Glut-2 (Mm00446224_m1); Pax6 (Mm00443072_m1); and Arx (Mm00545903_m1). Expression levels were normalized against 18S rRNA (Hs99999901_s1).

Ratiometric Analysis:

In addition to the relative quantification of individual genes, we also examined the differential expression of endocrine versus exocrine genes, as well as beta-cell vs. alpha cell genes in each group (ratiometric analysis). First the average of the triplicate wells for the numerator and denominator gene of interest was calculated. In this case, the gene ratios were calculated within individual groups. From the average gene values (Ct), we subtracted the average value of the housekeeping gene (18S). The resulting number is dCt. Then, the average of the adjusted numerator cycles was subtracted from the adjusted denominator cycles. Finally, as each cycle represents a doubling of reaction product, the fold difference was calculated by the following formula:

$$\text{Fold change} = 2^{-n}$$

where n is equal to the average difference of cycle numbers between numerator and denominator genes. Once these ratios were calculated for each gene combination in the control and experimental group respectively, we determined the ratio of the experimental value to the control value. In this way, we could examine ratiometric differences within each group and then between groups. An illustrative example of the method is provided below for a gene A/gene B ratio.

Group: PFC/Si

|        | Ct | 18s | dCt (Ct − 18s) |             |                  |
|--------|----|-----|----------------|-------------|------------------|
| Gene A | 20 | 12  | 8              |             |                  |
| Gene B | 30 | 14  | 16             | 8 − 16 = −8 | $2^{-(-8)} = 256$ |

Thus, the ratio of gene A to gene B in the PFC/Si group is 256. Similar calculations resulted in ratios of 32 in the standard control. We can conclude, therefore, that the ratio of gene A/gene B is 256/32=8 times higher in the PFC/Si than in the standard control group.

Oxygen Consumption:

Pancreatic buds were placed in a temperature controlled oxygen consumption rate (OCR) stirred micro-chamber system equipped with Ruthenium fiber optic oxygen sensors (Instech Laboratories, Plymouth Meeting, Pa.). This system measures declining oxygen concentration ($\Delta_c O_2$) with time. The probes were calibrated using room air, (210 μM oxygen) and 100 mM sodium sulfite (NaSO$^{3-}$) (Sigma-Aldrich Chemical Co., St. Louis, Mo.), which consumes all oxygen in the system through chemical binding with the sulfur. This was performed using five consecutive harvests of precursor buds. Duplicate runs of 3 buds per chamber were performed in three harvests, and one run of 6 buds in the fourth and fifth harvest. All measurements were performed in complete culture medium. The system was continuously stirred, thus maintaining oxygen equilibrium within the chamber. Since the chamber volume is known, the oxygen consumption could be determined from the linear slope of the $\Delta c O_2$ The slope (expressed as μM) was multiplied by the chamber volume (250 μL) to obtain the mols of oxygen consumed. This value, expressed in mol/min, was divided by 60 to obtain the mols of oxygen consumed per second.

Polarographic Microelectrode Oxygen Measurements:

On the day following harvest, murine pancreatic buds from control and PFC/Si culture conditions were utilized for measurement of tissue oxygen gradients. 3 pancreatic buds from each group were transferred into a 35 mm culture dish, either with standard plastic bottom or with a perfluorocarbon-silicone matrix bottom (3.36 ml of culture medium). Sequentially, each dish was placed in a microincubator (Harvard Apparatus, Boston, Mass.) affixed to the stage of a Zeiss inverted microscope, with 3.36 ml of fresh culture medium without sodium bicarbonate. The microincubator maintained the temperature at 37° C. for the duration of the measurements. In the absence of bicarbonate, the medium pH was maintained by 25 mM HEPES buffer. Evaporation during the measurements was minimal (<2% total volume). The oxygen microelectrodes utilized (Diamond General Inc, Ann Arbor, Mich.) had an average tip diameter of 8 µm. Each probe was subjected to a two-point calibration, first in nitrogen dissolved in culture medium (0%) and then by room air in culture medium (20.9%). Calibrations were performed at 37° C. to maintain thermal consistency.

For each measurement, an individual pancreatic bud was affixed to a glass pipette tip on one side of the microscope stage by vacuum patch clamp technique. The buds were allowed to equilibrate for 105 minutes, which is the calculated equilibration time of the system—the square of the diffusion path length (medium height) divided by the diffusion coefficient of oxygen through the medium ($2.1 E^{-0.05}$ $cm^2$/s). The oxygen microelectrode was affixed to the other side of the microscope stage in a robotic micromanipulator (Eppendorf) capable of precision movements in the x, y and z planes down to a resolution of 0.2 All electrode and temperature data were recorded through an analog data collection board interfaced with a laboratory PC via an RS-232 connection. Data collection software (DASYLab) was utilized to transform analog voltage signals to digital readouts for assessment of oxygen concentrations within the pancreatic buds.

Oxygen measurements were collected for two minute intervals by guiding the electrode normal to the surface into the tissue. An initial measurement was made at −250 µm relative to the surface with internal measurements made at 10 µm intervals from the surface to the core of the pancreatic bud (approximately 260 µm). Three individual measurements were performed per bud and three buds per group were utilized for oxygen measurements.

Quantification of Immunostaining:

Metamorph® imaging software (Molecular Devices Inc., Downington, Pa.) was used to quantify relative amounts of insulin and glucagon staining in every section. This imaging package allows for the accurate quantification of fluorescent signal in any biological tissue section. Positive areas were calculated as percentages by dividing positive pixel number/section by the total pixel number/section. Total positive volume percentages/bud were then calculated for all the sections of any given bud, according to the equation:

$$\frac{\sum_{1}^{n} P+}{\sum_{1}^{n} P_t}$$

Where n is the number of sections, Pt, is the total pixels and, P+, is the number of positive pixels for each specific hormone. The average percentages were calculated from the individual percentage values from each group.

Tissue Procurement and Culture:

Pancreatic buds from e9.5-e16.5 CBA×B6 embryos (noon of the day a vaginal plug is found is considered 0.5 days of gestation) were isolated and microdissected. Culture medium was GMEM (Invitrogen) supplemented with 0.1 mM MEM non-essential amino acids (Invitrogen), sodium pyruvate, 5% (v/v) new-born bovine serum, 5% (v/v) fetal calf serum, 0.1 mM 2-mercaptoethanol, penicillin (100 U/ml)/streptomycin (100 µg/ml) and L-glutamine (250 µM) (Invitrogen). Controls were plated in 12 mm, 0.4 µM Millicell inserts (typically 2 buds/insert) and incubated at 37° C. and 5% $CO_2$, either at 21% or 35% $O_2$. Buds assigned to the experimental group were plated in PFC/Si culture plate inserts (see FIGS. 5A-5B) and incubated at 37° C. and 5% $CO_2$ and 35% $O_2$.

Immunostaining and Image Analysis:

Explants were grown as above for 3 days and then fixed with 4% paraformaldehyde (30 min.), washed with PBS (30 min.) and frozen in O.C.T. compound (Sakura). Pancreatic rudiments were sectioned in their entirety (5 µm) and mounted with DAPI-vectashield (Vector). Guinea pig anti-insulin and rabbit anti-glucagon antibodies (BioGenex, ready-to-use solution) were used for double staining BrdU (Sigma) was added to the culture medium at a final concentration of 10 µM and kept overnight (and added freshly every day) before fixation. Rat anti-bromodeoxyuridine (BrdU) antibody (Accurate, 1:100 dilution) and FITC-conjugated hypoxyprobe (Chemicon, 1:100 dilution) were used for detection of proliferating cells and hypoxia, respectively. Rabbit antibodies against amylase (1:200), carboxypeptidase (1:200), E-cadherin (1:100) and Nestin (1:100) were obtained from Santa Cruz, Sigma, Zymed and Covance, respectively. All secondary antibodies were purchased from Molecular Probes (Invitrogen). METAMORPH® software was used to quantitate insulin and glucagon staining.

Real Time qRT-PCR.

Total RNA was purified using Qiagen kits (QIAShredder, RNeasy and DNase-free). The First-Strand system (Roche) was used to generate cDNA (random oligomers). Relative gene expression was calculated using Taqman assays in a 7500 Fast Real Time PCR cycler (Applied Biosystems, ABI). The $\Delta$Ct method for relative quantification was deemed optimal for this application. All assays (ABI) were designed to span exon-exon junctions, thus eliminating the possibility of genomic DNA contamination. qRT-PCR results are the average of several independent experiments, as indicated in the Results section. In addition, in each experiment each marker was analyzed in triplicates. Specific assay numbers are provided as supplementary information. Gene expression was normalized against 18S rRNA. This endogenous control has been validated in our system and proven extremely stable and more accurate over varying $O_2$ concentrations than other standards.

Statistical Analysis.

ANOVA tests were used to analyze variance between the means of the different groups ($P<0.05$). When more than two groups are compared, paired student's t-tests usually result in a higher probability of type I errors (i.e., when the null hypothesis is rejected even though it is true), hence the use of ANOVA. Standard error of the means (S.E.M) was used for all our analyses.

$O_2$ Diffusion Modeling:

3D Diffusion/Reaction theoretical modeling was performed on permutations of control and experimental culture systems using COMSOL v.3.2 finite element analysis software. Iterative solutions for concentration profiles were determined utilizing the time dependent solver. The modeling allowed us to examine the effect of multiple variables, including medium height, tissue proximity, perfluorocarbon volume fraction and external $O_2$ concentration. Our calculations were based on published diffusion coefficients for tissue and culture medium, as well as measured dimensions and $O_2$ consumption rates (OCRs) of mouse pancreatic buds. The validity of the models was confirmed by direct $O_2$ readings of pancreatic buds in vitro, using polarographic microelectrode-based techniques.

Insulin Measurement: Total protein was extracted from groups of 6-8 pancreatic buds, and insulin content measured using Mercodia ELISA kits.

Results.

PFC/Si Devices Ensure High Oxygenation Levels in e13.5 Pancreatic Buds:

We used dorsal pancreatic buds explanted at e13.5 as our primary model of in vitro differentiation. This point is within the period of maximal 0 cell specification in the developing mouse, and the effect of interventions on their in vitro spontaneous development can be readily quantified. 30 dorsal pancreatic buds pooled from e13.5 embryos (6 pregnant C57 females) were microdissected and measured. Their average dimensions were 449.7+/−78.5 μm×649.8+/−79.3 μm×450.1+/−79.1 μm. Average $O_2$ consumption rate was 8.95+/−0.75×10$^{-3}$ mol/m$^3$·s$^{-1}$. Variability between samples was <10%, despite using tissue from different harvests.

Traditional culture of pancreatic buds is done in inserts where the tissue rests atop a permeable membrane, barely bathed with the medium beneath. These "medium/air interface" conditions ensure acceptable oxygenation levels, but nutrient diffusion is suboptimal, growth is limited and medium needs to be replenished often to prevent desiccation. This is a cumbersome and very specialized culture system with few uses, if any, outside the area of developmental studies of small explants. Stem cell differentiation, particularly for large-scale therapeutic applications, will require standard expansion systems where cells are properly immersed in culture medium.

In order to replicate the air transfer restrictions of standard stem cell culture methods, while accommodating the special needs of our biological model (which requires a basal membrane to maintain the morphological integrity of the buds), we have modified the basal control conditions so that pancreatic buds sit on top of a permeable membrane but culture medium bathes them all around (up to 1 mm above the cells, see FIG. 5A). As it could be argued that the level of oxygenation in this "hybrid" system would be lower than in conventional settings, we added a second control where $O_2$ concentration is increased to 35% in the incubator. Mathematical modeling and direct in vitro measurements demonstrate that such adjustment results in oxygenation levels comparable to those of the "medium/air interface" conditions, while maintaining an adequate medium height to support nutrition, expansion and differentiation. Thus, we modeled three culture platforms: (a) Standard control (Millipore Teflon inserts cultured in conventional $O_2$ concentration in a 95% room air/5% $CO_2$ incubator); (b) High $O_2$ control (the above system cultured in the presence of 35% $O_2$) and (c) PFC/Si (where the bottom of the Millipore inserts was replaced by a 450 μm-thick Silicone/20% perfluorocarbon membrane), also cultured at 35% $O_2$ In both controls, the samples rest at the top of liquid-permeable Teflon membranes that suspend them above the plastic bottom, so that both their apical and basal regions are bathed with culture medium (FIG. 5A, top). PFC/Si membranes, in contrast, are liquid-impermeable. By resting atop these membranes, samples are bathed by medium just from the top, while directly exposed to environmental $O_2$ from the bottom (FIG. 5A, bottom). The mass transfer rate of $O_2$ to the cells is greatly enhanced in this system, as it is not limited by diffusivity through the culture medium.

Finite element modeling of the diffusion/reaction parameters of each culture environment was performed using COMSOL v3.2 software. These calculations were validated by experimental $O_2$ measurements throughout the tissue.

At the beginning of the culture (day 0), pancreatic buds cultured in standard control conditions (FIG. 5B, top) have overall oxygenation levels below 100 mm Hg, with large areas (depicted in white) below 0.1 mm Hg. This is generally considered the threshold of anoxia. Increasing the $O_2$ concentration from 21 to 35% in the standard culture system (FIG. 5B, middle) prevents anoxia and improves oxygenation, although not as much as in PFC/Si devices (FIG. 5B, bottom).

Figure 6A:
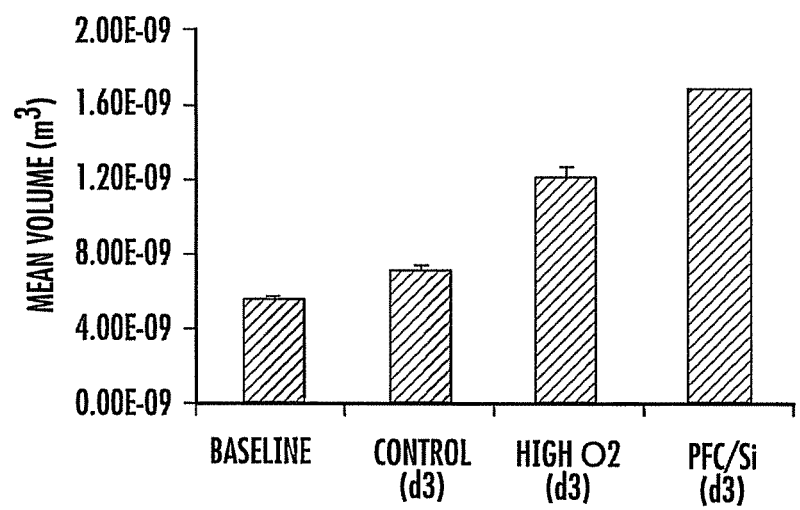
FIGS. 6A-6B show PFC/devices induce higher proliferation rates.
Figure 6B:
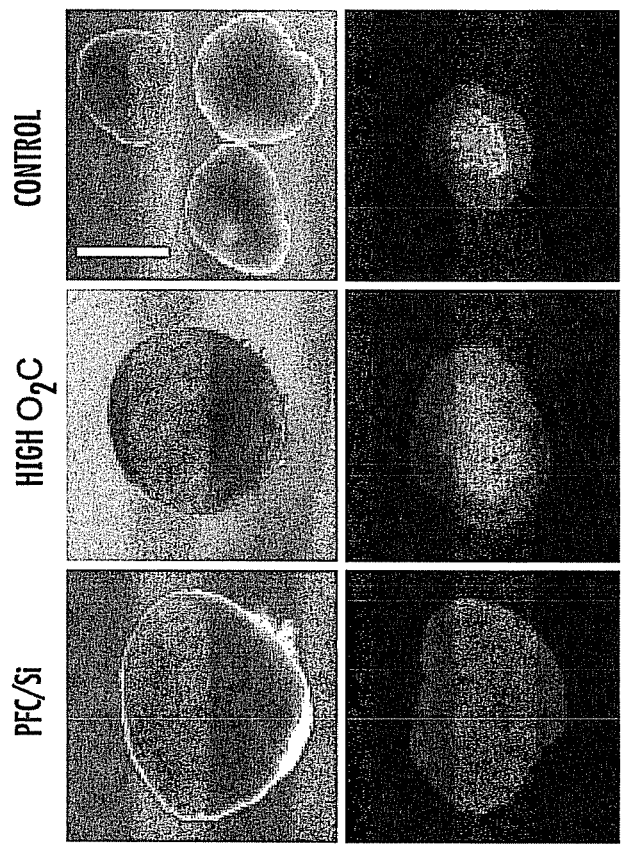

High $O_2$ Promotes the Growth of Pancreatic Buds in PFC/Si Settings without Hypoxia:

e13.5 dorsal pancreatic buds were explanted and cultured in normal conditions (standard control; n=13), 35% $O_2$ (high $O_2$ control; n=14) and PFC/Si membranes at 35% $O_2$ (experimental group; n=14). Maximal growth of the explants was observed at 72 h of culture. Longer periods (up to 1 week) did not result in additional expansion. Buds in the experimental group tripled their volume over the 3-day culture period. Explants kept at high $O_2$ alone also expanded significantly, but not as much (2-fold). Buds in standard conditions, finally, showed the least increase in size (1.1-fold) (FIGS. 6A and 6B, left column). Our theoretical calculations, adjusted for the increased size of the buds at 72 h, indicate that this growth is accompanied by a decrease in $O_2$ diffusion across the tissue. This was confirmed by the use of a histological probe for hypoxia in samples fixated after 3 days in culture. The hypoxyprobe binds to protein adducts formed when tissue is exposed to $O_2$ partial pressures of <10 mm Hg 58. Midpoint sections of representative samples of each group show large hypoxic areas in buds cultured both in standard and high $O_2$ conditions, but not in those plated in PFC/Si devices (FIG. 6B, right column). In conclusion, our studies confirm that PFC/Si platforms prevent hypoxia and ensure high oxygenation levels in our test system.

Figure 7:
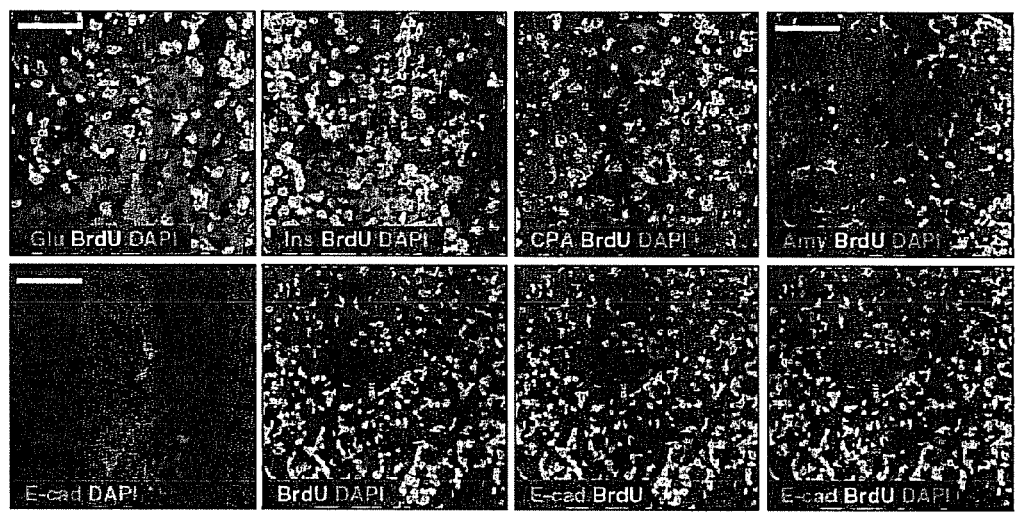
FIG. 7 is a series of photographs showing PFC/Si-induced growth is due to replication of undifferentiated epithelial cells. Confocal immunofluorescent analysis of pancreatic buds cultured for three days in PFC/Si devices in the presence of BrdU (green). Blue, DAPI nuclear counter-staining. Top row: in red, clockwise from the left: Glucagon (Glu), Insulin (Ins), Carboxypeptidase A (CPA) and Amylase (Amy). Few terminally differentiated cells had BrdU co-staining. Bottom row: BrdU (green), DAPI (blue) and E-cadherin (E-cad) (red) staining of PFC/Si cultured buds, shown as two-channel combinations (microphotographs 1, 2 and 3) and 3-channel combination (microphotograph 4). Most of the cells in the bud are E-cadherin+ (epithelial). Proliferation occurs preferentially within the E-cadherin+-undifferentiated population. Scale bars: 50 µm (Glu, Ins, CPA) and 75 µm (Amy, E-cad).

PFC/Si-induced growth is due to replication of undifferentiated epithelial cells. In order to determine the nature of the cells responsible for the proliferation observed during culture, we added bromodeoxyuridine (BrdU) to the culture medium for the entire length of the experiment (72 h), and then fixed, sectioned and immunostained the samples. Co-expression of BrdU and markers of terminal differentiation (Insulin, Glucagon, Amylase and Carboxypeptidase A) was rare in all the groups, as shown in FIG. 7. This observation indicates that there is no significant replication of mature epithelial cells. It is known that mesenchymal E-cadherin−/Nestin+ cells are intermingled with epithelial cells at this stage of development. These cells, however, turned out to be scarce and largely BrdU-negative in all the groups. Most of the BrdU incorporation was found to be localized in E-cadherin+/differentiation marker-cells (FIG. 7, bottom row). In summary, our results indicate that proliferation occurs preferentially in undifferentiated epithelial cells that do not mature during the course of the experiment.

Figure 8A:
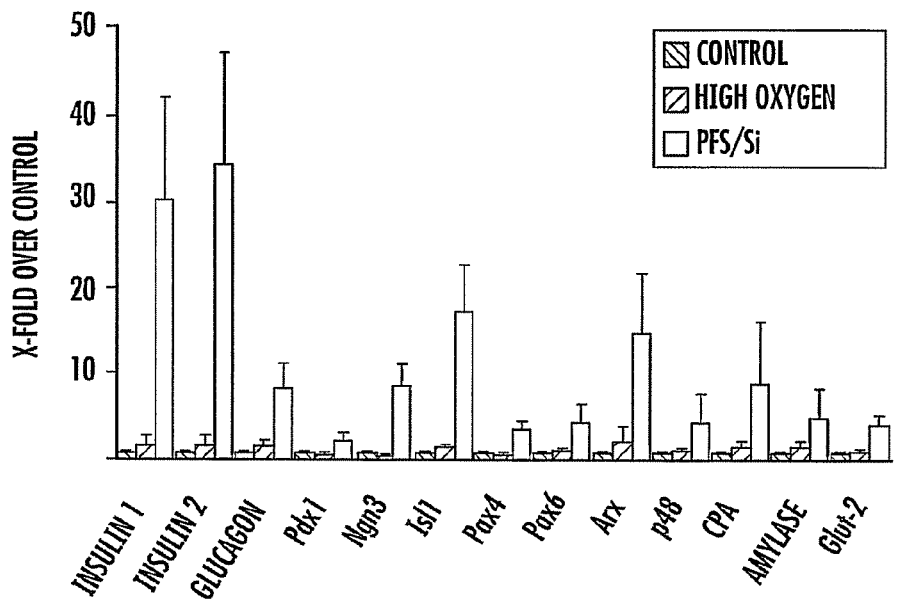
FIGS. 8A-8C show that culture in PFC/Si platforms promotes endocrine differentiation.

Differentiation is Greatly Enhanced in PFC/Si Devices Compared to Standard and High $O_2$ Controls:

e13.5 dorsal pancreatic buds were harvested and cultured as above. At day 3, the explants were lysed for RNA isolation and protein extraction, or fixed for immunohistochemical analysis. A panel of genes involved in the progression of pancreatic differentiation and β cell maturation was tested by qRT-PCR in 7 independent experiments (2-3 buds/group). As shown in FIG. 8A, all genes examined are upregulated in the PFC/Si group compared to the standard control: Insulin 1 (30-fold), Insulin 2 (34-fold), Glucagon (8-fold), Pdx1 (2-fold), Ngn3 (8-fold), Isl1 (4-fold), Pax4 (14-fold), Pax6 (3.5-fold), Arx (15-fold), P48 (4.5-fold), Carboxypeptidase A (9-fold), Amylase (5-fold) and Glut-2 (4-fold). Surprisingly, the values observed in the high $O_2$ control were barely above those of the standard control, and in some cases even lower.

Figure 8B:
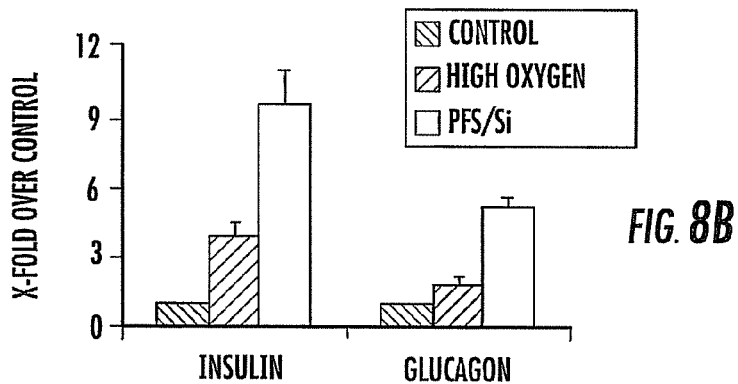
Figure 8C:
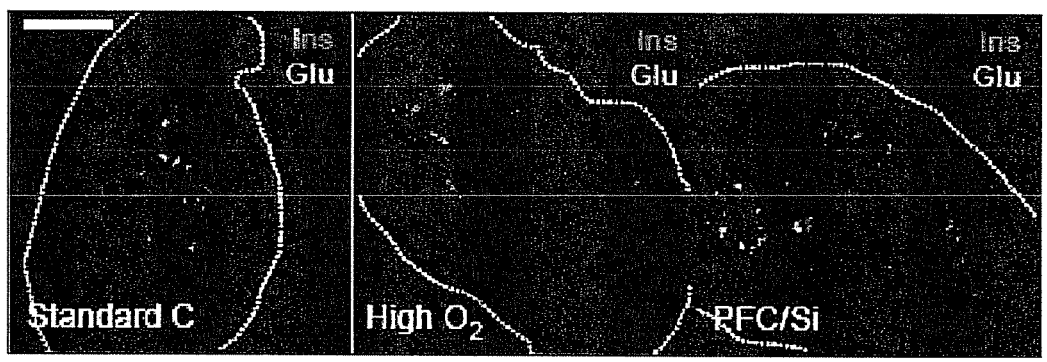

Differences between the PFC/Si group and the controls were statistically significant for Insulin 1 (P=0.025) and 2 (P=0.025), Glucagon (P=0.020), Ngn3 (P=0.017), Pax4 (P=0.039), Pax6 (P=0.037) and Glut-2 (P=0.025), but not for the pancreatic endocrine markers Pdx1 (P=0.07), Isl1 (P=0.06) and Arx (P=0.09) or the exocrine markers P48 (P=0.45), carboxypeptidase A (P=0.43) and amylase (P=0.34). Metamorph® analysis of immunofluorescence-labeled buds (n=5 independent experiments, 3 buds/group) confirmed the up-regulation of Insulin and Glucagon, the two major endocrine hormones observed at this point of development. As represented in FIG. 8B, Insulin+ staining in PFC/Si buds is nearly 10-fold that of standard controls (2.5-fold that of high $O_2$ controls). Similarly, Glucagon+ signal was 5 times more abundant in the experimental group than in conventional settings (3-fold that of high $O_2$ controls). ANOVA tests show that differences between the PFC/Si and the standard control group (P=0.01 and 0.001 for insulin and glucagon, respectively), but not between the two control groups, are statistically significant. Representative sections of buds cultured in each condition, shown in FIG. 8C, show that clusters of insulin- and glucagon-producing cells were thicker and denser in PFC/Si than in control buds.

Since the majority of these new endocrine and exocrine cells that differentiated during in vitro culture arose from post-mitotic progenitor cells (FIG. 7), it could be concluded that the increased rates of growth and differentiation are two distinct effects of culture in PFC/Si devices. We sought additional proof by examining PFC/Si-induced differentiation in the absence of proliferation. Prior to culture in each condition, we treated freshly microdissected e13.5 buds with mitomycin C (MMC), a potent inhibitor of cell division. Even if not as dramatically as before, differentiation was still significantly higher (2- to 6-fold for endocrine cell markers) in the experimental group compared to both controls. This observation confirms that the enhancement of endocrine differentiation in PFC/Si-cultured buds is independent from the parallel increase in their proliferative capacity.

Figure 9A:
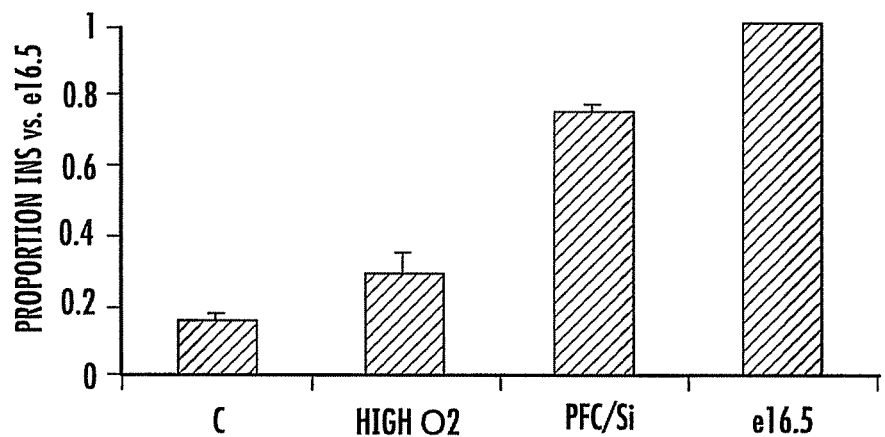
FIGS. 9A-9B are graphs showing insulin content and gene expression profiles of PFC/Si-cultured e13.5 buds approximate that of e16.5 buds.
Figure 9B:
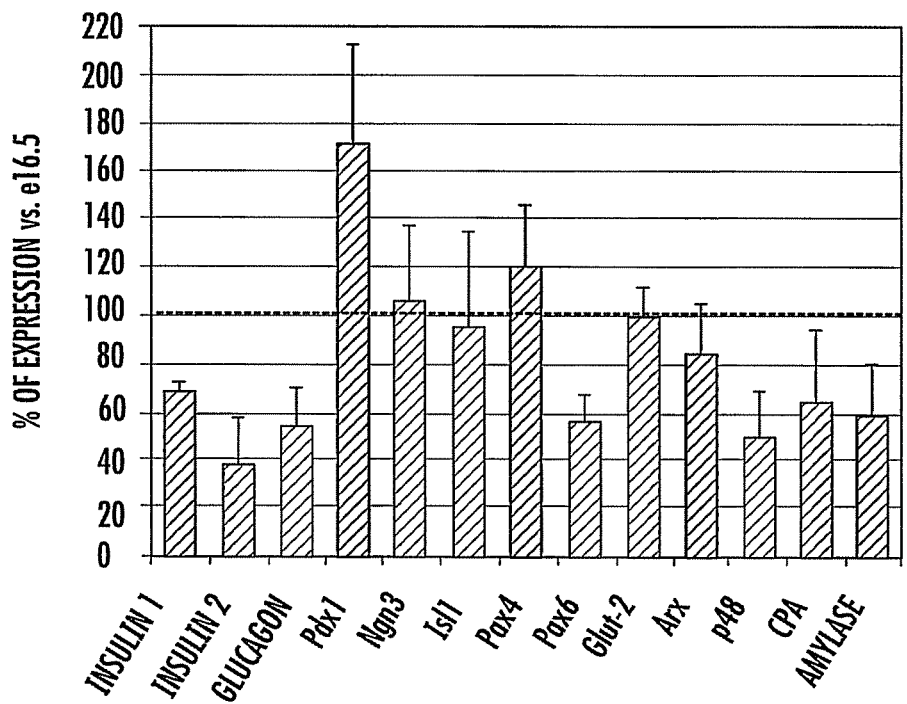

In vitro maturation in PFC/Si devices closely mimics in vivo development: In order to assess the extent to which buds cultured in PFC/Si approximate in vivo levels of differentiation, pancreatic buds obtained at e16.5 (a time point corresponding to e13.5 buds+3 days of ex vivo development) were lysed for RNA and protein extraction (n=4 independent experiments). These values were compared to those previously obtained from PFC/Si-cultured buds. Total insulin content of buds cultured for 3 days in PFC/Si was nearly 80% that of freshly explanted e16.5 buds, compared to 30% and 15% in the high $O_2$ and standard control groups, respectively (FIG. 9A). This observation was confirmed and further expanded by qRT-PCR, where the above panel of genes was run in the e16.5 harvests and compared to the 7 PFC/Si in vitro experiments. FIG. 9B presents gene expression profiles of the PFC/Si group expressed as a percentage of that determined for e16.5. Most of the differences between the PFC/Si group and e16.5 are statistically insignificant (P>0.05), suggesting that in vitro maturation occurred at in vivo rates.

Figure 10A:
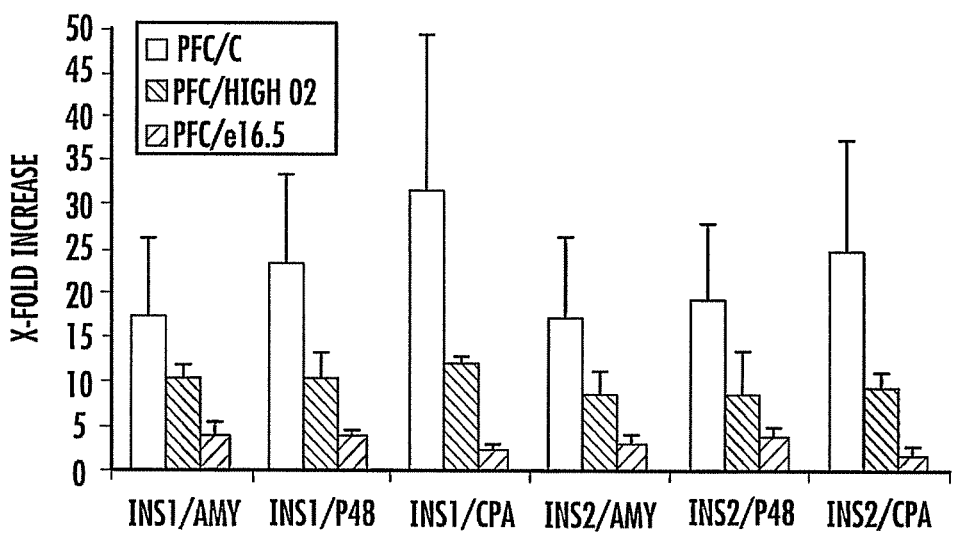
FIGS. 10A-10B are graphs showing PFC/Si induces preferential endocrine over exocrine and β cell over α cell differentiation. Ratiometric analysis of gene expression in the PFC/Si group compared to e16.5 buds (striated boxes) as well as standard (grey boxes) and high oxygen (closed boxes) controls. Values are represented as x-fold increase of the net ratio for each pair of genes in the PFC/Si group over that of the other three groups.
Figure 10B:
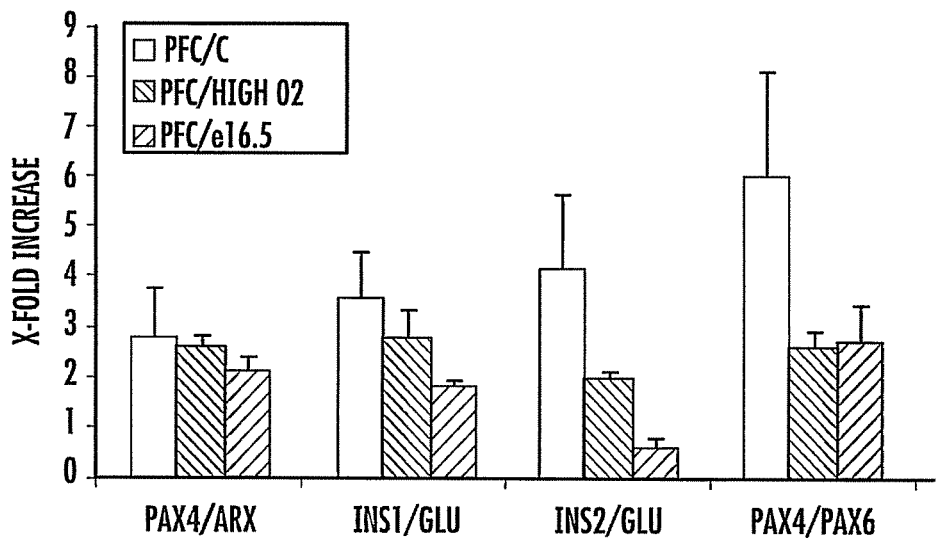

PFC/Si Promotes Endocrine Over Exocrine and β-Over α-Cell Differentiation:

One possible interpretation of the above results is that a better method of $O_2$ delivery simply promotes overall differentiation. We hypothesized, however, that our method for enhanced oxygenation would preferentially induce the specification of endocrine cells, as their $O_2$ demands exceed greatly those of exocrine tissue. To test this hypothesis, and based on the qRT-PCR data presented above, we calculated the ratios of endocrine-to-exocrine and .beta.-to-.alpha. cell differentiation. As shown in FIG. 10, these ratios are consistently higher in the PFC/Si group than in the two in vitro controls (up to 30-fold for endocrine/exocrine and 2-3 fold for β-to-α cell ratios) and even the e16.5 pancreatic buds (2-3 fold for both types of ratios).

Discussion:

Success at efficiently differentiating pancreatic endocrine tissue from a renewable source of cells could have immediate therapeutic applications for the treatment of type I diabetes. However, current methods for the in vitro specification of 0 cells are still inefficient. We hypothesized that a better recapitulation of the physiological environment of 0 cells (of which oxygenation is a key component) may be conducive to higher differentiation yields.

Our results confirmed the above hypothesis in a mouse model of pancreatic development, but only when air was delivered in a basal-apical fashion. Increasing the concentration of $O_2$ in the incubator in standard culture conditions did not result in any significant up-regulation of endocrine differentiation. While the "oxygen sandwich" effect could also be achieved with membranes made of silicone alone, those that included PFC in their composition proved superior in preliminary experiments. Expression of endocrine markers (Glucagon, Insulin 1, Insulin 2 and Pax4) was between 2- and 5-fold higher in PFC/Si than in the silicone alone group, with no significant differences in exocrine gene differentiation or proliferation markers. The advantages of PFC/Si over silicone alone in terms of $O_2$ diffusion were additionally confirmed by direct measurements using non-invasive optical $O_2$ biosensors. Hence, we opted for PFC/Si devices for all subsequent experiments.

Our data show an unequivocal enhancement of endocrine differentiation, with Insulin 1 and 2 expression levels exceeding 30-fold those of buds cultured in standard conditions, be it at 21% or 35% $O_2$. All markers of endocrine differentiation were also upregulated, including Ngn3 (a marker of pro-endocrine cell types), Glucagon and Pax-6 (a cells), Isl1 (endocrine cells), Pax4 (pro-β cells), Glut-2 and Pdx1 (pro-β cells) and Pax6 (pro-β cells). Although the increase in Pdx1 levels observed in PFC/Si-cultured buds over the standard control was a seemingly modest 2-fold (6-fold over high $O_2$ control), it must be noted that, other than throughout the duct epithelium, expression of this gene is just starting to reappear around this time in arising β cells.

It could be argued that our results are merely a reflection of better culture conditions, rather than a preferential effect of enhanced oxygenation on endocrine differentiation. However, the observed up-regulation of exocrine markers in PFC/Si cultured bud was statistically insignificant. The above hypothesis was further disproved by calculating the quotients between endocrine (Insulin 1 and 2) and exocrine (Carboxypeptidase A, Amylase and p48) markers. Within endocrine cells, we also determined Insulin/Glucagon, Pax4/Pax6 and Pax4/Arx ratios. The latter has been shown to be important at the crossroads between α and β cell segregation from a common progenitor cell (excess of Pax4 over Arx will result in a cell differentiation, whereas the opposite will lead towards the generation of a cells). Similarly, expression of Pax6, but not Pax4, is normally associated to a cell specification at this stage of development. In all the experiments conducted, the PFC/Si group showed invariably higher endocrine-to-exocrine and β-to-α cell differentiation ratios than the two in vitro controls. Surprisingly, they were even higher than in freshly explanted e16.5 pancreatic buds, which represent a valuable control of in vivo differentiation.

An enhanced growth rate was also observed when using PFC/Si devices. BrdU incorporation studies show that the majority of the newly generated cells were epithelial (E-cadherin+). BrdU, however, was very rarely seen in terminally differentiated cells (Amylase+, Carboxypeptidase+, Insulin+ or Glucagon+). This indicates that most of the newly differentiated endocrine or exocrine cells arose from progenitors that were already quiescent at the beginning of the experiment. Our data, therefore, support the notion that PFC/Si matrices have two distinct effects on e13.5 pancreatic buds: (a) enhanced proliferation of epithelial cells that do not differentiate during the course of the experiment; and (b) enhanced endocrine differentiation of a post-mitotic subpopulation of progenitor cells. The independence between proliferation and differentiation was further confirmed by experiments where, despite a mitomycin C-induced arrest of proliferation, endocrine differentiation was still enhanced. Among the differentiation pathways directly influenced by $O_2$ tension, Notch is of utmost relevance for pancreatic development. This pathway is generally involved in the maintenance of an undifferentiated state, and its down-regulation is key for the initiation of the endocrine differentiation cascade. Under hypoxic conditions, the hypoxia inducible factor 1α (HIF-1α) is stabilized and interacts with the intracellular domain of Notch, activating this signaling cascade. In this context, it follows that higher oxygenation would destabilize HIF-1α, which in turn would inhibit Notch signaling, promoting endocrine differentiation. This would be consistent with the observation that the second and most significant wave of β cell specification (secondary transition) is concurrent with the initiation of blood flow within the pancreatic buds, long after endothelial cells first appear in the tissue.

However (as we also see in our in vitro model), higher oxygenation can also induce proliferation of non-endocrine cell types, a behavior that cannot be explained by the HIF-1/Notch pathway. This typically happens through the generation of reactive oxygen species (ROS), which have been shown to participate as signal transducers in numerous biological processes.

Figure 11:
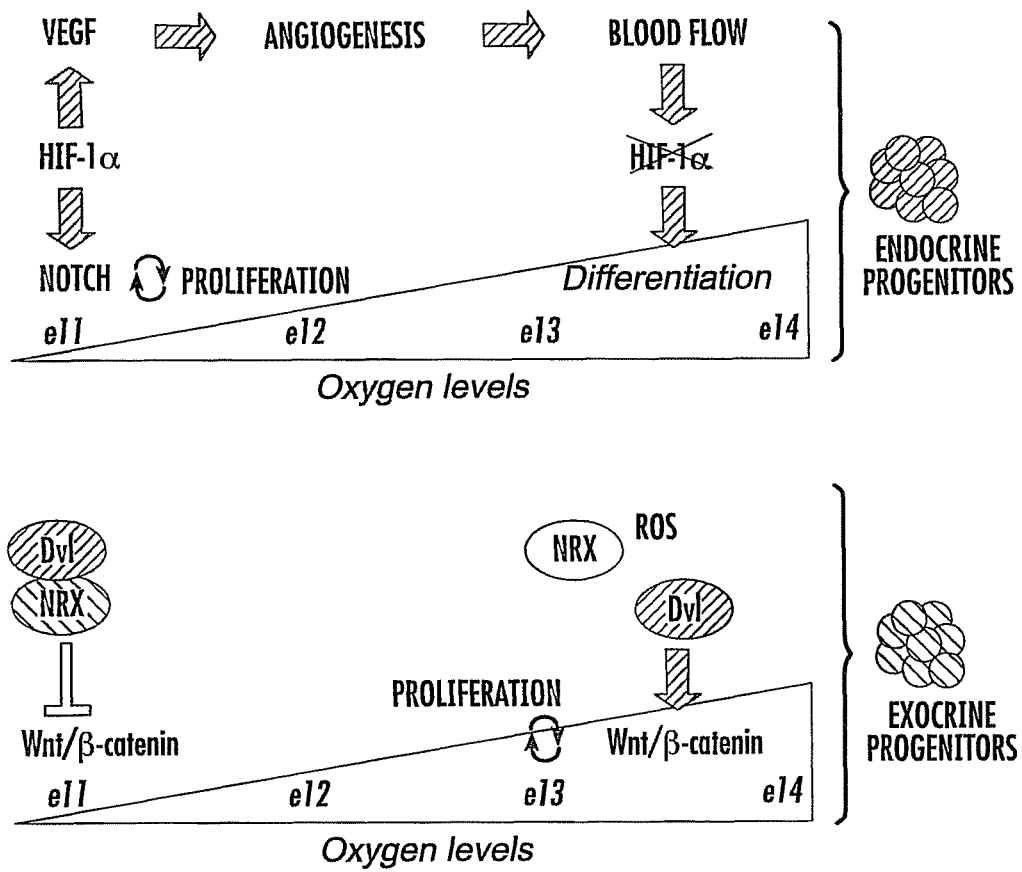
FIG. 11 is a schematic representation of a hypothetical model to explain the role of $O_2$ in pancreatic development. According to the hypothesis hypoxic conditions present in the pancreas prior to the initiation of blood flow would favor the HIF-1α-mediated activation of Notch in endocrine progenitor cells, promoting their self-renewal but largely preventing their differentiation. HIF-1α stabilization in hypoxic conditions also induces VEGF-mediated angiogenesis, which will eventually lead to the initiation of blood flow at around e13.5. Enhanced oxygenation of pancreatic tissues at that point will destabilize HIF-1α, resulting in Notch down-regulation and differentiation of endocrine cell types. Exocrine progenitor cells, in contrast, may react to higher $O_2$ levels by activating the Wnt/β-catenin pathway via NRX sequestration by ROS. This would promote their expansion throughout the rest of embryonic development.

A model that fits the experimental evidence is presented in FIG. 11. Hypoxic conditions present until e13.5 would theoretically favor the Notch-dependent proliferation of pancreatic progenitors. Since these conditions also promote angiogenesis in a HIF-1-dependent manner, the initiation of blood flow and subsequent oxygenation would: (a) arrest Notch signaling in endocrine progenitor cells (thus allowing a massive wave of endocrine differentiation around that time); and (b) activate Wnt/β-catenin signaling in exocrine progenitor cells (thus triggering sustained acinar cell proliferation). According to this hypothesis, PFC/Si devices (but not hypoxic control conditions) would, to some extent, mimic the two independent effects of angiogenesis in different cell subsets of the developing pancreas. The testing of this hypothesis is presently the subject of several lines of research in our laboratory.

The observation that high $O_2$ concentrations per se did not enhance differentiation over basal levels demonstrates that standard methods of air delivery are ill-suited to sustain growth and differentiation of cell aggregates. After three days in culture, buds cultured in high $O_2$ had a very significant incidence of hypoxia, which was not observed in PFC/Si-cultured explants. Notably, improved $O_2$ delivery was not accompanied by oxygen-induced stress. Preliminary multiplex analyses shows differential activation of AKT phosphorylation (survival signal) and suppression of c-jun, NF-kB and ERK (stress activated kinases) in the PFC/Si group compared to both controls Conclusions:

To date, most attempts at differentiating islets from stem cells have focused only on their molecular environment. Our results emphasize the importance of providing developing progenitor cells with the right physiological environment, opening a new avenue of research that timely complements parallel advances in the field. In short, this work: (1) presents evidence of a direct relationship between oxygenation and pancreatic endocrine cell differentiation, whose molecular mechanism is presently under study; and (2) describes a novel cell culture tool designed to deliver $O_2$ in a physiological-like fashion, which could be of immediate use in the development of more efficient islet differentiation protocols from adult and/or embryonic stem cells.

Example 7

Effect of PFC/Si Conditions in the Culture of Embryoid Bodies Derived from Human Embryonic Stem (huES) Cells Objective: To assess the influence of enhanced oxygenation (as provided by PFC/Si devices) on the expression of pancreatic endocrine markers in huES cell-derived embryoid bodies.

HuES cells organize in embryoid bodies when cultured in conditions that do not favor their attachment (such as hanging drops or bacterial Petri dishes). These embryoid bodies (EBs) give rise to a variety of tissues of all three embryonal layers, namely endoderm, ectoderm and mesoderm. Insulin-positive cells have been detected, even at a low percentage, in EBs spontaneously differentiated for about 3 weeks. The aim of this experiment was to determine whether culture in PFC/Si dishes would result in higher levels of expression of pancreatic endocrine genes.

Methods:

A confluent T180 flask of H10 huES cells at passage 30 was trypsinized and cells allowed to form EBs in serum-free conditions for 20 days. RNA samples were taken at that time to establish a baseline. EBs were then distributed in four groups, namely: control (regular Petri dishes), control high oxygen (the same but at 35% $O_2$), PFC/Si (10 cm PFC/Silicone plates) and PFC/Si high oxygen (the same but at 35% $O_2$). These were cultured for 5 more days, at which time RNA samples were taken for qRT-PCR analysis.

Results:

The results of this preliminary experiment can be summarized as follows:

1. After 3 days in culture, glucagon gene expression is highest in the PFC/Si High oxygen group (5-fold over day 20), followed by PFC/Si (4-fold). Control and high oxygen controls have increases of 2.734 and 3.2-fold, respectively.

2. Glucagon expression cannot be detected in any group after 5 days in culture, with the exception of the PFC/Si High oxygen (11-fold increase over day 20). Therefore, only PFC/Si platforms are permissive for long-term expression of glucagon in this particular biological system.

3. Insulin expression cannot be detected either at the day 20 baseline or after 3 days of culture (in any condition). The same applies to 5 days of culture with the exception of PFC/Si high oxygen. This is the only group where insulin expression can be detected (average Ct of 3 samples=34.88). Considering that the threshold for detection is Ct=40, in the less optimistic scenario the amplification observed would correspond to 40−34.88=5.12; $2^{5.12}$=34-fold over any other condition.

4. While Pdx1 expression levels are comparable in the four groups after 3 days in culture (1.5-2.8-fold over day 20 levels), at day 5 it can only be detected in the PFC/Si High $O_2$ group, with a 6.35-fold increase over that of day 20.

In summary, PFC/Si conditions, especially at high $O_2$, seem to be most permissive for the spontaneous expression of genes of endocrine pancreatic development in EBs. This is consistent with the working hypothesis, already postulated in the main body of this application, that pancreatic endocrine differentiation is highly promoted by enhanced oxygenation. Experiments aimed at testing this in two directed huES cell differentiation protocols are presently underway.

Example 8

Effect of PFC/SI Conditions in the Culture of Primary Non-Human Primate Hepatocytes To assess the level of expression of albumin, a hepatocyte differentiation marker, on non-human primate hepatocytes cultured in regular conditions vs. PFC/Silicone devices.

Experimental Design:

NHP liver cells at passage 3 were cultured either on 6-well plates (100,000 cells plated in 2-ml media) or on PFC/Si plates (51,000 cells plated in 1 ml media), both pre-treated with fibronectin. In both culture conditions, plates were incubated either at regular (21%) or high (35%) $O_2$ concentrations. RNA samples were taken at day 5 of culture and albumin expression measured by qRT-PCR (Applied Biosystems).

Results:

After 5 days in culture, hepatocytes cultured in PFC/Si devices tended to associate in cell aggregates attached to the surface. Control cells, in contrast, remained in a monolayer.

Discussion:

Although preliminary, the above results seem to indicate that culture in PFC/Si devices improves the expression of a marker (albumin) associated with the maintenance of a hepatocyte phenotype. This result would be of great significance for the field of in vitro hepatocyte expansion, as one common effect observed in cultured hepatocytes is their loss of differentiation markers with time. Interestingly, high oxygen did not result in improved albumin expression when using PFC matrices, suggesting that, while PFC has a generally positive effect of the culture of metabolically demanding tissues (especially 3D aggregates), the specific $O_2$ concentration that will give the best results needs to be adjusted on a case by case basis.

Example 9

Effect of Culturing Mouse Neurospheres in PFC/Si Devices

Neurospheres are free-floating 3D aggregates generated by neural stem cells (NSCs) in vitro. These are self-renewing, multipotent cells with the ability to differentiate into to all neural populations (Bez A, et al. Brain Res. Dec. 12, 2003; 993(1-2):18-29.) This is the culture method of choice to expand neural stem cells prior to their differentiation, and a tool for the study of neural biology and development (Campos L S. J Neurosci Res. Dec. 15, 2004; 78(6):761-769). As any other 3D cell aggregate, neurospheres are subject to mass transfer limitations, especially related to oxygen diffusion (Plotnikov E Y, et al. Bull Exp Biol Med. January 2006; 141(1): 142-146). When they reach a critical size, they must be disaggregated and passaged to avoid hypoxia-related effects on their viability and rate of proliferation. Based on our experience with embryonic pancreatic buds, we set up to test the hypothesis that culture of Neurospheres in PFC/Si devices would result in enhanced proliferation rates.

Methods

Murine neurospheres were cultured in DMEM/F-12 medium supplemented with B27, Penicillin/Streptomycin, bFGF and EGF. In these conditions, aggregates grow up to 150-250 μm, after which mass transfer rates become limiting. Neurospheres at this average size, typically indicates a need for trypsinization. Control neurospheres were placed in E-well plates in low (5%) regular (21%) or high (35%) $O_2$ incubator; experimental conditions were similar but the neurospheres were placed on PFC/Si dishes. Culture was carried out for 48 h. A pulse of BrdU was added at the beginning of the experiment to study proliferation.

Results:

Neurospheres cultured in PFC/Si dishes, both at regular and high $O_2$ concentrations, volumetrically expanded up to 10 times more than relevant controls (up to 1 mm of diameter) in a 48 h period. Higher proliferation rates were confirmed by BrdU staining (FIGS. 2A-2D). Proliferation was minimal in both groups at low $O_2$.

Figure 2:
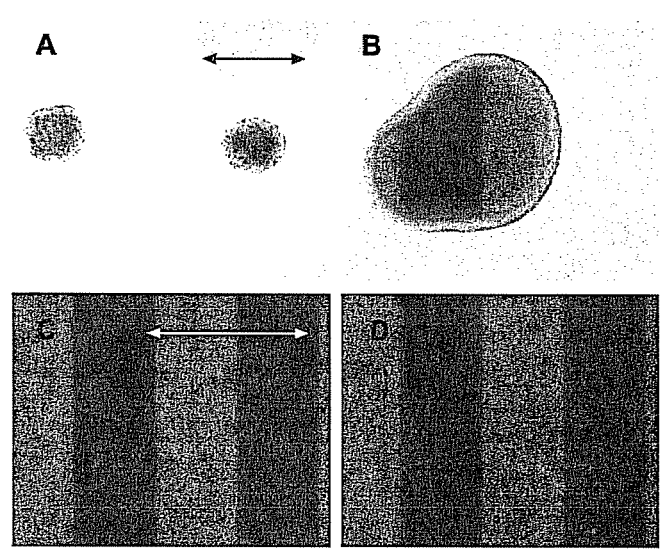
FIGS. 2A-2D are scans of photographs showing.

Discussion:

PFC/Si dishes dramatically enhance the proliferation of neural stem cells in neurospheres. BrdU incorporation studies show that most of the proliferative activity is detected superficially in control aggregates (FIG. 2C). This consistent with the hypothesis that, being oxygen-dependent, proliferation will occur rarely in the hypoxic core of the neurospheres. neurospheres. PFC/Si culture, in contrast, allows for the continued growth of the neurospheres without oxygen diffusion limitations up to a higher threshold. Unlike those in the control group, proliferation can also be seen in the core of the neurospheres cultured in PFC/Si (FIG. 2D). In summary, the culture system circumvents oxygen transfer limitations inherent to conventional methods, and allows for a dramatic increase of the proliferation rate of neural stem cells in vitro.

Example 10

A Physiological Pattern of Oxygenation Using Perfluorocarbon-Based Culture Devices Maximizes Pancreatic Islet Viability and Enhances Beta Cell Function Conventional culture vessels are not designed for physiological oxygen ($O_2$) delivery. Both hyperoxia and hypoxia—commonly observed when culturing cells in regular plasticware—have been linked to reduced cellular function and death. Pancreatic islets, used for the clinical treatment of diabetes, are especially sensitive to sub- and supra-physiological $O_2$ concentrations. A result of current culture standards is that a high percentage of islet preparations are never transplanted because of cell death and loss of function in the 24-48 h post-isolation. Here we describe a new culture system designed to provide quasi-physiological oxygenation to islets in culture. The use of dishes where islets rest atop a perfluorocarbon (PFC)-based membrane, coupled with a careful adjustment of environmental $O_2$ concentration to target the islet physiological $pO_2$ range, resulted in dramatic gains in viability and function. These observations underline the importance of approximating culture conditions as closely as possible to those of the native microenvironment, and fill a widely acknowledged gap in our ability to preserve islet functionality in vitro. As stem cell-derived insulin-producing cells are likely to suffer from the same limitations as those observed in real islets, our findings are especially timely in the context of current efforts to define renewable sources for transplantation.

METHODS

Use of Human Tissue Material:

Investigations with human tissues were preceded by University of Miami Institutional Review Board (IRB) approval.

Human Islet Isolation:

Human islet preparations were processed at the Diabetes Research Institute cGMP Core according to standard methods described elsewhere (24, 46).

Figure 12:
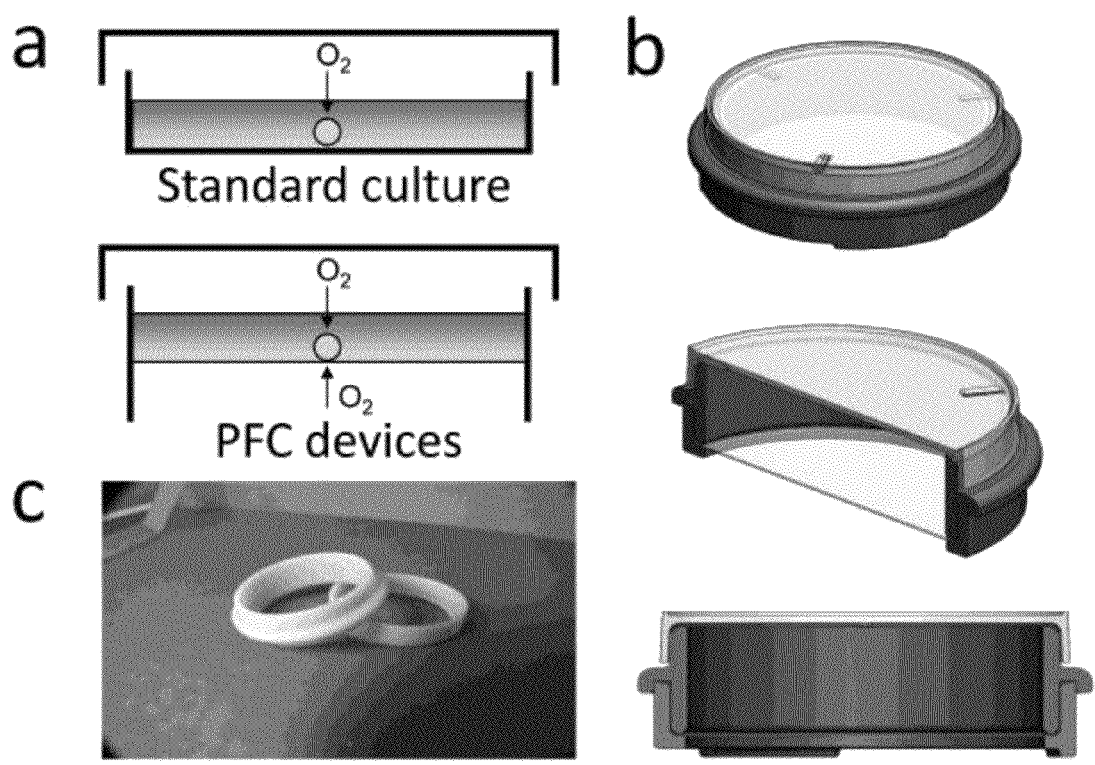
FIG. 12 illustrates an embodiment of a PFC/PDMS-based device. (A) Diagram of the oxygen flow in standard (top) and PFC (bottom) culture systems. Typical culture dishes exhibit a unidirectional flow of air from the top, whereas PFC/PDMS membrane-based devices allow for bi-directional oxygenation both from the top and the bottom, through a gas-permeable, liquid impermeable membrane. (B) Diagram showing the design of the 35 mm PFC/PDMS culture dish. Inner and outer rings are held together by an interference fit. Once assembled, three feet elevate the dish off the surface to allow for bottom-up aeration through the PFC/PDMS membrane. (C) Photograph of a resin-based rapid PFC/PDMS dish prototype.

35 mm PFC/PDMS Dish Manufacture:

We set out to build a mass-producible, disposable 35 mm diameter prototype in which the inner and outer rings are held together by an interference fit, and the latter has three legs that elevate the membrane 1 mm off the surface to allow circulation of air from underneath (FIG. 12). Membranes were extruded by Specialty Silicone Fabricators (Paso Robles, Calif.) according to our specifications. A two-part polydimethylsiloxane (PDMS) [RTV615 Part A (938.7 g); RTV615 Part B (312.9 g) (GE Silicones)] and Perfluorooctyltriethoxysilane (Alfa Aesar) (408.9 g) were mixed to obtain a 0.012" (305 μm+/−12 μm)×13" (33 cm)×600" (1,524 cm) roll from which discs could subsequently be punched. Rapid prototyping was done with the Objet Eden 250 3D printing system. Prototypes were manufactured with VeroWhite resin to check fit and function. Advanced models were made by Computer Numerical Control (CNC)-assisted precision machining Injection molding was done with Noryl HNA033, an unfilled modified polyphenylene ether resin designed to withstand several autoclave cycles and gamma irradiation sterilization. The injection molding of the inner and outer rings of the 35 mm prototype was done at ProtoMold (Maple Plain, Minn.). The assembly process was done at Biorep Technologies (Miami, Fla.). For quality control, the assembled dish was placed on a tension meter jig and tension read with a Newman SRMeter1. Tension had to be within the 16-40 N/cm range.

Diffusivity studies: $O_2$ spot sensors (PreSensGmBH, Regensberg Germany) were affixed with epoxy to the center of the bottom surface of wells in a standard 24 well culture plate (VWR Inc, Marietta, Ga.). 3 mm PDMS or PFC/PDMS membranes were subsequently fit into the wells atop the sensors, using quick-drying PDMS along the outer edges to insure an air-tight seal. As a control, some sensor wells were filled with 60 μL Hanks Balanced Salt Solution (HBSS, Invitrogen, CellGro). After equilibration at 38 mm Hg $O_2$ (5%), the entire sensor rigging was transferred to the upper stage of an incubator set to standard 95% Room Air/5% $CO_2$ culture conditions. Taking into account vapor pressure differences, this translates to a $pO_2$ of 142 mm Hg. Care was taken not to agitate the well-plate to avoid convective disturbances. Additionally, the time of exposure to the temperature difference between the incubator and the room (approximately 12° C.) was never greater than 5 seconds, so as to minimize thermal effects. $O_2$ partial pressure was measured in the system until the signal reached an equilibrium point at the new $pO_2$ setting of 142 mm Hg. Data points were recorded every 15 seconds for the length of the experiment. Our modeling assumed that (a) diffusion was 1D through the height of the measured compound, as the sides were treated as impermeable to $O_2$; (b) effects due to diffusion through plastic and the edge seal were minimal; and (c) temperature shifts from moving the apparatus were negligible.

Theoretical Modeling:

A retrospective analysis of islet size distributions from 184 human isolations was performed. The total volume of each count and the contribution of each size range to the total volume was determined as previously described (7). The majority of the tissue volume (77% pre-Ficoll and 80% post-purification in layer 1) fell in the range of 100-300 μm, with the largest percentage measuring between 150-200 μm. This volume distribution was utilized for finite element modeling to maintain the largest tissue percentage [Islet Equivalents (IEQs) between 100-300 μm] at or near physiological $pO_2$ while minimizing anoxia and hyperoxia.

The $O_2$ consumption rate (OCR) of each preparation prior to plating was assessed using triplicate aliquots of 500 IEQs in a stirred chamber $O_2$ measurement device (Instech Labs, Plymouth Harbor, Pa.). 2D Diffusion/Reaction theoretical modeling was performed on permutations of control and experimental culture systems using COMSOL v.3.3 finite element analysis software.

Glucose-Stimulated Insulin Release (GSIR):

Glucose stimulated insulin release was done by aliquoting 100 IEQs suspended in a Sephadex G10 slurry within 10 mL microchromatography columns. After an equilibration incubation in low glucose (2.2 mM)-modified Krebs buffer containing 0.1% w/v BSA, 26 mM sodium bicarbonate and 25 mM HEPES buffer, sequential 1 hour incubations were performed in low (2.2 mM), high (16.6 mM) and low (2.2 mM) buffers. Samples were collected for insulin analysis at the end of each hour following the pre-incubation. Insulin was quantified using the Mercodia Human Insulin ELISA (Winston Salem, N.C.). The insulin data utilized was the difference in total insulin production per 100 IEQs between the high glucose and first hour of low glucose stimulation (Delta). In our experience, this value strongly correlates with full mass subrenal capsular transplant outcome in athymic nude mice.

$O_2$ Consumption Rate (OCR):

The DNA-normalized index of OCR was calculated using the BD Oxygen Biosensor as previously described (17). Briefly, triplicate 200 μL aliquots of 500 IEQs each suspended in either a modified Krebs buffer containing low (2.2 mM) or high (16.6 mM) glucose concentrations were placed in individual wells of the BD Biosensor. Dry, medium containing and sodium sulfite controls were also run in triplicates. After equilibration at 37° C., fluorescence measurements were taken every 5 minutes for 16 hours (ex: 485 em: 620). The early increase (between minutes 15-50) in fluorescence signal is indicative of the rate of $O_2$ depletion in each well.

qRT-PCR:

Total RNA was purified using miRNA Mirvana kit (Life Technologies, Grand Island, N.Y.). Random oligomers were used to generate cDNA with the High Capacity Reverse Transcription kit (Life Technologies, Grand Island, N.Y.). Relative expression of selected markers was calculated using Taqman® assays in Applied Biosystems thermal cyclers (Life Technologies, Carlsbad, Calif.). The 7900HT model was used to run Taqman® Low Density Array (TLDA) pre-designed cards (apoptosis). The ΔCt method for relative quantification was employed for all calculations.

Animal Studies:

Animal procedures were done under protocols approved by the University of Miami Institutional Animal Care and Use Committee. Athymic nude mice (5-6 week old, Harlan Laboratories, Indianapolis, Ind.) were housed in virus antibody-free rooms with free access to autoclaved water and food at the Division of Veterinary Resources. Personnel at the Translational Models Core of the Diabetes Research Institute performed all surgical procedures. A single streptozotocin (stz) injection induced selective destruction of islet β-cells and onset of diabetes. Animals were monitored and insulin pellets used if needed to maintain the overall health of the animals prior to transplantation. Under general anesthesia, the left kidney was externalized and a small puncture made in its capsule. Islets were injected under in a minimal volume of saline. The muscle/fascia was sutured with cat gut 4-0 and the skin closed with surgical staples. Buprenorphin was administered subcutaneously to alleviate postsurgical pain. After transplantation, recipients were followed-up with blood glucose measurements to monitor graft function.

Statistical Analyses:

The averaged results of in vitro assessments are expressed as the mean fold control ±standard deviation (SD) for the purpose of easily understood quantification. For statistical analysis, the raw data were utilized in non-parametric rank sum tests. When calculating the standard deviation of ratios, the following formula was utilized:

$$R \times \sqrt{(cv(X)^2 + cv(Y)^2)} \quad (1)$$

where R represents the ratio, $$\frac{X}{Y},$$

cv(X) is the variance of the numerator, and cv(Y) the variance of the denominator.

The raw data was utilized in the Mann-Whitney (rank sum) statistical test, assuming non-Gaussian distribution. The Mann-Whitney test utilizes the parametric raw data assigning a rank to each value independent of the group association. These ranks are then summed for each group and the difference between the sums dictates the p value, where a larger difference correlates with lower p value. A $p \leq 0.05$ was considered significant. Values of $p \leq 0.01$ were considered highly significant.

Kaplan-Meier survival analysis with log-rank (Mantel-Cox) and Gehan-Breslow Wilcoxon tests for significance were performed on transplant data.

Results

A Device for Enhanced Oxygenation:

We have designed a culture device in which cells and tissues can receive O2 both from the top (diffusing through the medium) and the bottom (across a perfluorohydrocarbon-silicone, or PDMS/PFC, membrane) (FIG. 12). Perfluorohydrocarbons, or PFCs, are inert compounds made of carbon-fluorine chains. Because of this molecular configuration, they can bind and transfer O2 with ease. The O2 solubility of PFCs is about 50 times higher than that of medium, which is superior to that of hemoglobin under certain conditions (4). Their O2 diffusivity is also considerably higher that of water or medium (37). Computerized mathematical modeling (COMSOL), as well as direct in vitro measurements (18) show that our system maximizes the volume of tissue exposed to physiological pO2.

O2 Diffusivity Through PFC/PDMS Exceeds that Measured on PDMS Alone Membranes:

In order to address whether PFC/PDMS membranes had any advantage over those made of PDMS alone, we conducted diffusivity studies as indicated in Methods. The average diffusivity value calculated for the "PDMS alone" membrane was $3.9 \times 10^{-5} \pm 2.97 \times 10^{-6}$ cm$^2$/s (n=4), which fell within the range of average values for silicone in the literature. In contrast, the average diffusivity calculated for the 20% v/v PFC/PDMS composition was $6.46 \times 10^{-5} \pm 4.51 \times 10^{-6}$ cm$^2$/s (n=4), nearly 70% higher than that of the silicone (p<0.01). Therefore, PFC/PDMS membranes have higher O$_2$ diffusivity than those manufactured exclusively with PDMS. The advantage of adding PFC was further proven using a biological system (embryonic pancreatic buds) in vitro, as previously described (18).

Figure 13:
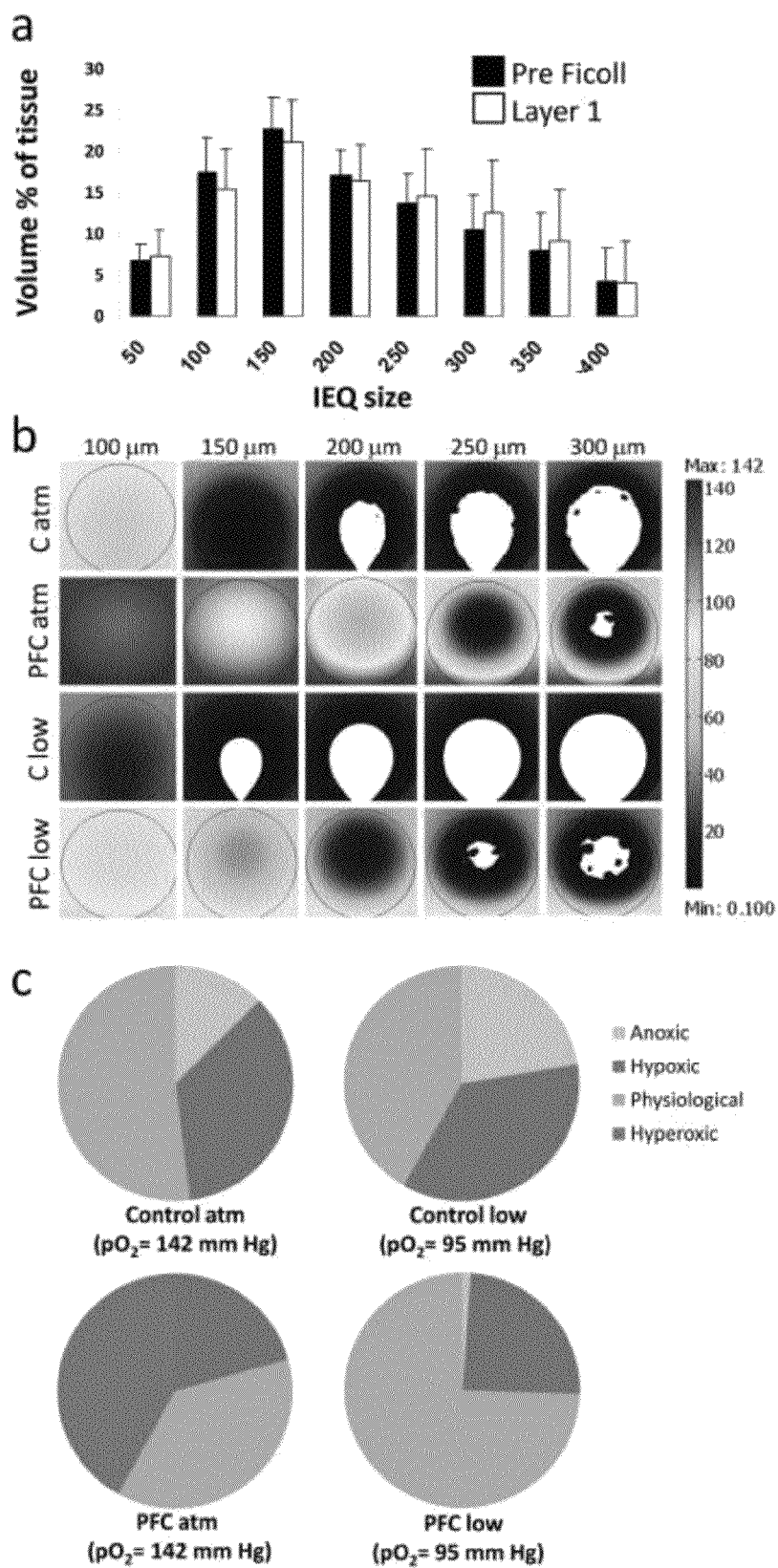
FIG. 13 shows theoretical oxygen diffusion modeling. (A) Retrospective analysis (n=184) of the size distribution pattern in islet preparations. The largest percentage of islets (77% pre-Ficoll and 80% layer 1 post-purification) is in the 100-300 µm range, with a majority of them measuring between 150 and 200 µm. The latter figure was used for all subsequent finite element modeling calculations. (B) Theoretical modeling of all four groups: C atm (control dishes, atmospheric 21% [$O_2$]), PFC atm (PFC/PDMS dishes, atmospheric 21% [$O_2$]), C low (control dishes, 12.5% [$O_2$]) and PFC low (PFC/PDMS dishes, 12.5% [$O_2$]). Islet sizes modeled are indicated in the top row (100-300 µm, in 50 µm increments). The color scale indicates p$O_2$ levels from 0.1 mm Hg (deep blue) to 142 mm Hg (deep red). (C) Distribution of regions (anoxic, hypoxic, physiological and hyperoxic; see definitions in main text) in each one of the four groups. The "PFC low" group [PFC/PDMS dishes at 95 mm Hg (12.5%), bottom right] exhibits the largest tissue volume percentage at physiological levels (74.5%) as well as the lowest percentages of hyperoxic and anoxic tissue volume (0 and 1.2%, respectively).

Determination of the Human Islet Normoxic Range Using PFC/PDMS Dishes:

Islets cultured at 21% O$_2$ in regular dishes are known to receive suboptimal oxygenation (41). Due to the intrinsic limitations of conventional culture devices, mere changes in the incubator's O$_2$ concentration still generate diffusion gradients that are detrimental for islet cell function and viability. PFC/PDMS dishes, in contrast, allow for a better targeting of a desired physiological range. Theoretical modeling of O$_2$ diffusion through islets sized 150-200 μm (FIG. 13A) was done using COMSOL v.3.3 finite element analysis software. We modeled O$_2$ diffusion through islets of different sizes plated in both regular plasticware and PFC/PDMS dishes. Environmental O$_2$ concentrations spanned a range from 8% (low) to 21% (regular). FIG. 13B shows the results of these calculations for four representative culture groups, namely: plasticware in atmospheric [O$_2$]; PFC/PDMS in atmospheric [O$_2$]; plasticware at low [O$_2$]; and PFC/PDMS at low [O$_2$]. According to these models, a maximal volume of tissue at physiological O$_2$ levels is reached when the islets are placed in PFC/PDMS dishes at an external pO$_2$ of 63-95 mm Hg (approximately 8-12.5% O$_2$), depending on the OCR. The ranges examined within the tissue were: critically anoxic (<0.1 mm Hg, no OCR), hypoxic (>0.1 mm Hg<0.4 mm Hg, OCR rapidly decreasing), physiological (>0.4 mm Hg<100 mm Hg) and hyperoxic (>100 mm Hg). As shown in FIG. 13B, the model indicates that islets cultured at reduced pO$_2$ (95 mm Hg, or 12.5%) on PFC/PDMS ("PFC low") have the highest percentage of tissue volume (~75%) within the physiological O$_2$ range. In this setting there was almost no critical anoxia, and hyperoxia was undetectable. In contrast, all other groups had either a significant percentage of both anoxic and hypoxic regions [control plasticware, both at atmospheric (21%) and low (12.5%) O$_2$ concentration] or a large hyperoxic portion of tissue [PFC/PDMS at atmospheric (21%) O$_2$ concentration]. All modeling was done at a standard plating density of ~175-200 IEQs/cm$^2$.

Targeting of a Physiological O$_2$ Range Maximizes Islet Viability and Function:

In order to test our theoretical calculations, we set up a series of experiments with isolated human islets. Individual preparations were analyzed according to several criteria, including β cell fractional viability (24) and OCR index (17). Taken together, these criteria are generally predictive of islet cell function in humans, and help establish retrospectively whether a preparation is "good" or "bad". The improvement observed in aliquots from low quality preparations cultured in PFC/PDMS dishes (n=5), was marginal compared to samples in control conditions. These preparations had very low OCR and glucose stimulation indices, and were largely irresponsive regardless of the culture conditions. However, 8 samples were considered to be of fair/good quality according to the above parameters. Aliquots of these samples were plated in either regular dishes (control) or PFC/PDMS devices (PFC), both at normal (21%) and low (8-12.5%) O$_2$ concentrations.

Figure 14:
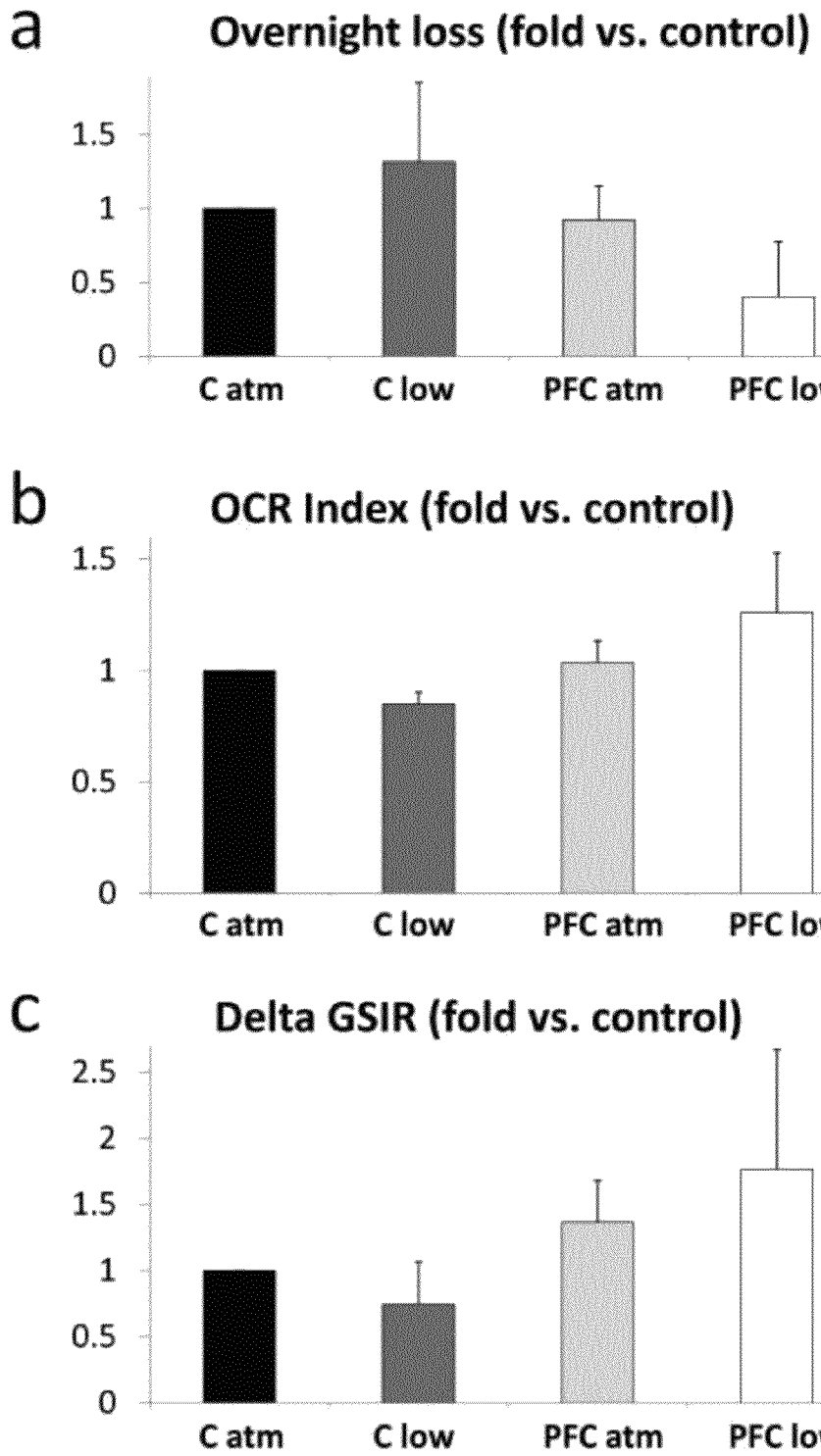
FIG. 14 demonstrates that human isolated islets exhibit higher viability and function when cultured at physiological p$O_2$ in PFC/PDMS dishes. (A) Overnight islet loss (-fold vs. control). C atm: Regular culture dishes, 21% (atmospheric) [$O_2$]; C low: Regular culture dishes, low [$O_2$]. The latter percentage was adjusted within the 8-12.5% range based on the OCR of each individual preparation in order to target the maximal volume percentage at physiological p$O_2$ within the tissue; PFC atm: PFC/PDMS dishes, 21% (atmospheric) [$O_2$]; PFC low: PFC/PDMS dishes, low [$O_2$] (see range above). n=8 independent human islet preparations. The difference in viability between C atm (regular conditions) and PFC low (maximal tissue volume at physiological p$O_2$) is statistically significant (P<0.01). (B) Oxygen consumption rate (OCR) index (-fold vs. control). Groups are as above. n=8 independent human islet preparations. The difference in OCR between C atm (regular conditions) and PFC low (maximal tissue volume at physiological p$O_2$) is statistically significant (P<0.01). (C) Glucose stimulated insulin release (Delta GSIR). Groups are as above. n=5 independent human islet preparations. The difference in Delta between C atm (regular conditions) and PFC low (maximal tissue volume at physiological p$O_2$) had a P=0.05. Error bars: Standard deviation (SD).

As mentioned earlier, the latter was shown to be the optimal concentration range to target physiological islet oxygenation (~40 mm Hg) using the PFC/PDMS system. 24 h after plating the aliquots in each of the four conditions, we analyzed islet loss (FIG. 14A), OCR index (FIG. 14B) and glucose-stimulated insulin release (GSIR) (FIG. 14C). Our data show that islets cultured in PFC platforms perform significantly better than those kept in regular conditions: When normalizing against the control group at 21% $O_2$ (C atm=1), cell loss was 1.2+/−0.78 in the low $O_2$ control group (C low), 0.91+/−0.13 in the PFC/PDMS group at 21% $O_2$ (PFC atm) and only 0.53+/−0.45 in the PFC/PDMS group at low $O_2$ (PFC low) (FIG. 14A). The difference in viability between C atm (regular conditions) and PFC low (maximal tissue volume at physiological $pO_2$) was statistically significant (P<0.01). Similarly, when using C atm as a normalizer (=1), OCR was 0.8+/−0.01 in C low, 1.09+/−0.05 in PFC atm and 1.3+/−0.11 in PFC low (FIG. 14B). Once again, the difference in OCR between C atm (regular conditions) and PFC low (maximal tissue volume at physiological $pO_2$) was statistically significant (P<0.01). Finally, the GSIR delta normalized against the value obtained in C atm (=1) was 0.75+/−0.321 in C low, 1.22+/−0.25 in PFC atm and 1.37+/−0.17 in PFC low (FIG. 14C). These Delta values translate into relative GSIR indices of 1 (C atm), 0.68+/−0.10 (C low), 1.91+/−0.25 (PFC atm) and 1.94+/−0.79 (PFC low). Statistical analyses of both metrics showed that the PFC low group was better than conventional culture (P=0.05). In summary, survival and function were higher when adjusting the environmental $O_2$ concentration to better target the islet physiological range.

A Trend for Earlier Diabetes Reversal in PFC/PDMS-Cultured Islets:

The marginal mass transplantation model in diabetic mice is particularly suited for the purpose of analyzing the potential benefits of any given treatment (43). Transplantation of a small number of islets (500-1000) under the kidney capsule leads to the reversal of hyperglycemia, but typically there is a measurable delay from the time of implantation. If an intervention is effective, time to reversal is reduced. This model allowed us to assess the effects of pre-transplantation culture (24 h) of human islet preparations using PFC/PDMS devices.

Following isolation, human islets were allowed to recover overnight in regular conditions, and then separated in two aliquots: one was kept in standard dishes at 21% $O_2$ and the other placed in PFC/PDMS dishes at 8-12.5% $O_2$ (final concentration calculated based on the baseline OCR of each preparation). As mentioned earlier, the latter range sustains the maximal volume of the tissue at physiological $pO_2$ when using PFC/PDMS dishes.

24 h later, islets were aliquoted for transplantation (3 mice/group, 1000 islets/animal) and in vitro studies. The OCR was consistently higher (1.85 vs. 1.43) in the PFC/PDMS group, which is in line with our previous results. This parameter is highly predictive of function after transplantation (17), with higher indices normally indicating faster diabetes reversal times upon transplantation in mice. Similarly, the Glucose Stimulated Insulin Release (GRIR) "delta" (high minus low 1) was in average 2-fold higher in the PFC group than in controls.

Figure 15:
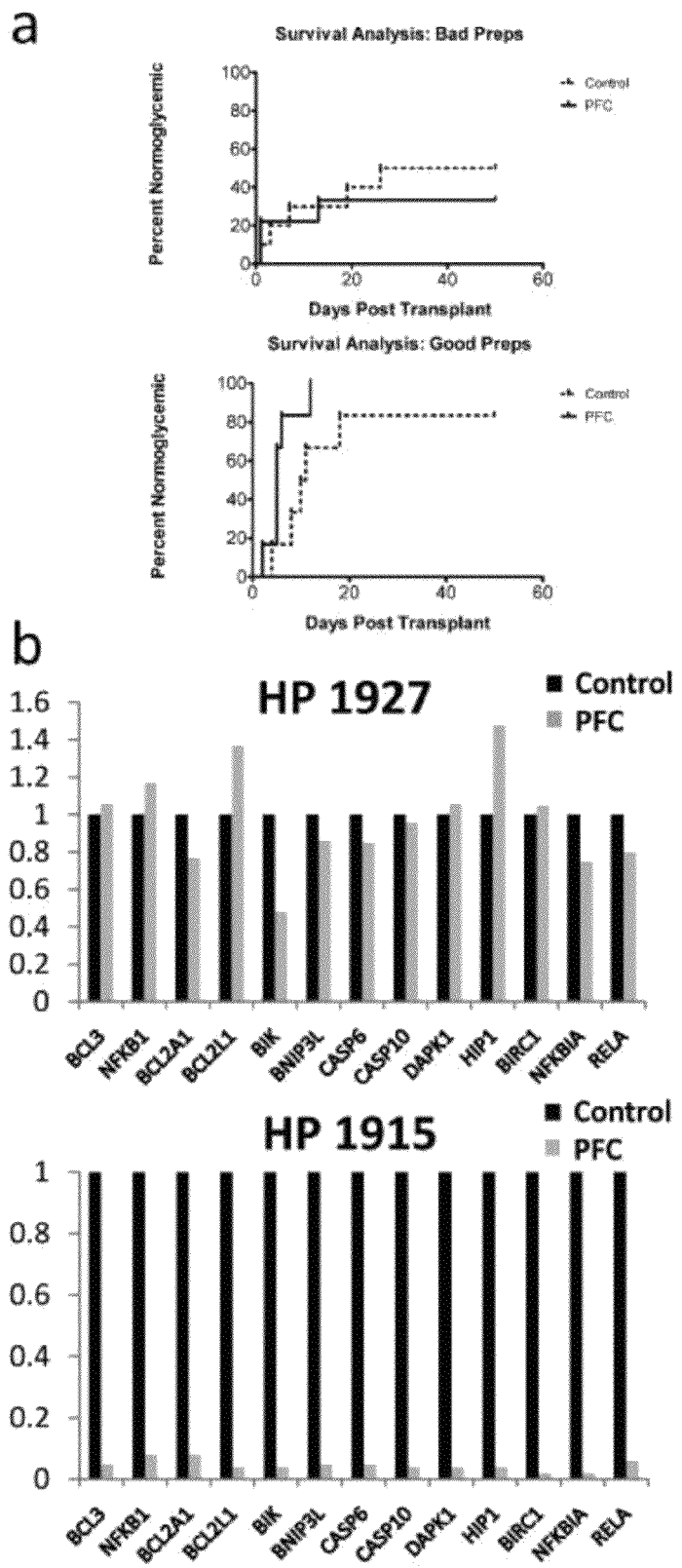
FIG. 15 demonstrates that human isolated islets exhibit higher viability and function when cultured at physiological p$O_2$ in PFC/PDMS dishes. (A) In vivo test of function of human islet preparations cultured in either PFC/PDMS-low oxygen (PFC group) or regular conditions atmospheric [$O_2$] (control group). Kaplan-Meier analyses of the gain of normoglycemia vs. time after transplantation of a marginal mass of islets into stz-treated, diabetic mice, are shown for the experiments using poor islet preparations (top) and those using good ones (bottom). (B) Poor islet preparations cannot be rescued by optimized oxygenation conditions. A Taqman® Low Density Array (TLDA) qRT-PCR analysis of a panel of genes involved in apoptosis is presented to exemplify the differences between a good preparation (HP 1915) and a bad one (HP 1927). In the latter, culture in PFC/PDMS dishes and low oxygen prevents the up-regulation of pro-apoptotic genes observed when placing an aliquot of the same preparation in control conditions (regular dishes, atmospheric [$O_2$]). In contrast, HP1927, a bad preparation with marginal GSIR readings, showed no difference in apoptosis between regular and oxygen-optimized conditions. This suggests that islets may have had a substantial degree of apoptosis before the placement in the two culture conditions, which culture in the optimized one could not revert.

The outcome of transplantation experiments is represented in FIG. 15. Based on in vitro metrics of viability, the preps were retrospectively grouped into either "rapid reversal" or "delayed/no reversal". In the first group, there was a clear trend (P=0.10) towards greater percentage of diabetes reversal (100% vs. 80%), defined as 5 consecutive days of blood glucose <200 mg/dL. Additionally, there was a trend toward earlier reversal times in the PFC group (5 days vs. 10.5 days), despite the small n (5 experiments). The in vivo outcomes coupled with the in vitro assessments indicate that preparations with poor basal in vitro performance typically are not rescued by culture in the PFC/PDMS. Conversely, preparations with in vitro performance that correlates with rapid reversal in the full mass bioassay, are improved in both their in vitro performance and in the marginal mass setting. Additional evidence was obtained from Taqman®-based Low Density Array (TLDA) cards designed to quantitatively measure the expression of a panel of 94 genes involved in apoptosis, which has been already proven to be at the root of hypoxia-induced islet cell death (19,39). The analysis of samples representative of a "good" preparation (HP1915) and a "bad" one (HP1927) is presented in FIG. 15B. Culture of HP1915 islets in PFC/PDMS dishes reduced the expression of pro-apoptotic genes by an entire order of magnitude vs. controls (15B, bottom panel). In contrast, the relative expression of these genes was comparable in both groups when using a bad preparation (HP1927, 15B, top panel). Absolute levels of expression were highly elevated in HP1927 vs. HP1915, suggesting that, for the most part, these islets were irreversibly apoptotic. In summary, our studies demonstrate that: (a) human islets exhibit enhanced survival and function when cultured in PFC/PDMS dishes; (b) this means of culture is translated in faster diabetes reversal times when islets are transplanted in immunodeficient, diabetic mice; and (c) culture in PFC/PDMS dishes cannot improve the viability of poor quality islet preparations.

REFERENCES

1. Avgoustiniatos, E. S.; Colton, C. K. Effect of external oxygen mass transfer resistances on viability of immunoisolated tissue. Ann. N.Y. Acad. Sci. 831:145-167; 1997.
2. Barshes, N. R.; Wyllie, S.; Goss, J. A. Inflammation-mediated dysfunction and apoptosis in pancreatic islet transplantation: implications for intrahepatic grafts. J. Leukoc. Biol. 77(5):587-597; 2005.
3. Bellin, M. D.; Kandaswamy, R.; Parkey, J.; Zhang, H. J.; Liu, B.; Ihm, S. H.; Ansite, J. D.; Witson, J.; Bansal-Pakala, P.; Balamurugan, A. N.; Papas, K.; Sutherland, D. E.; Moran, A.; Hering, B. J. Prolonged insulin independence after islet allotransplants in recipients with type 1 diabetes. Am. J. Transplant. 8(11):2463-2470; 2008.
4. Biro, G. P.; Blais, P. Perfluorocarbon blood substitutes. Crit. Rev. Oncol. Hematol. 6(4):311-374; 1987.
5. Brandhorst, D.; Brandhorst, H.; Hering, B. J.; Bretzel, R. G. Long-term survival, morphology and in vitro function of isolated pig islets under different culture conditions. Transplantation 67(12):1533-1541; 1999.
6. Brown, D. A.; MacLellan, W. R.; Laks, H.; Dunn, J. C.; Wu, B. M.; Beygui, R. E. Analysis of oxygen transport in a diffusion-limited model of engineered heart tissue. Biotechnol. Bioeng. 97(4):962-975; 2007.
7. Buchwald, P.; Wang, X.; Khan, A.; Bernal, A.; Fraker, C.; Inverardi, L.; Ricordi, C. Quantitative assessment of islet cell products: estimating the accuracy of the existing protocol and accounting for islet size distribution. Cell Transplant 0.18(10):1223-1235; 2009.
8. Carlsson, P. O.; Kozlova, I.; Andersson, A.; Roomans, G. M. Changes in intracellular sodium, potassium, and calcium concentrations in transplanted mouse pancreatic islets. Transplantation 75(4):445-449; 2003.
9. Carlsson, P. O.; Palm, F.; Mattsson, G. Low revascularization of experimentally transplanted human pancreatic islets. J. Clin. Endocrinol. Metab. 87(12):5418-5423; 2002.

10. Chase, H. P.; Ocrant, I.; Talmage, D. W. The effects of different conditions of organ culture on the survival of the mouse pancreas. Diabetes 28(11):990-993; 1979.

11. Cobianchi, L.; Fornoni, A.; Pileggi, A.; Molano, R. D.; Sanabria, N. Y.; Gonzalez-Quintana, J.; Bocca, N.; Marzorati, S.; Zahr, E.; Hogan, A. R.; Ricordi, C.; Inverardi, L. Riboflavin inhibits IL-6 expression and p38 activation in islet cells. Cell Transplant. 17(5):559-566; 2008.

12. Coppola, T.; Beraud-Dufour, S.; Antoine, A.; Vincent, J. P.; Mazella, J. Neurotensin protects pancreatic beta cells from apoptosis. Int. J. Biochem. Cell Biol. 40(10):2296-2302; 2008.

13. Dionne, K. E.; Colton, C. K.; Yarmush, M. L. Effect of hypoxia on insulin secretion by isolated rat and canine islets of Langerhans. Diabetes 42(1):12-21; 1993.

14. Fenjves, E. S.; Ochoa, M. S.; Cechin, S.; Gay-Rabinstein, C.; Perez-Alvarez, I.; Ichii, H.; Mendez, A.; Ricordi, C.; Curran, M. A. Protection of human pancreatic islets using a lentiviral vector expressing two genes: cFLIP and GFP. Cell Transplant. 17(7):793-802; 2008.

15. Fornoni, A.; Pileggi, A.; Molano, R. D.; Sanabria, N. Y.; Tejada, T.; Gonzalez-Quintana, J.; Ichii, H.; Inverardi, L.; Ricordi, C.; Pastori, R L Inhibition of c-jun N terminal kinase (JNK) improves functional beta cell mass in human islets and leads to AKT and glycogen synthase kinase-3 (GSK-3) phosphorylation. Diabetologia 51(2):298-308; 2008.

16. Fraker, C.; Ricordi, C.; Inverardi, L.; Dominguez-Bendala, J. Oxygen: a master regulator of pancreatic development? Biol. Cell 101(8):431-440; 2009.

17. Fraker, C.; Timmins, M. R.; Guarino, R. D.; Haaland, P. D.; Ichii, H.; Molano, D.; Pileggi, A.; Poggioli, R.; Presnell, S. C.; Inverardi, L.; Zehtab, M.; Ricordi, C. The use of the BD oxygen biosensor system to assess isolated human islets of langerhans: oxygen consumption as a potential measure of islet potency. Cell Transplant. 15(8-9):745-758; 2006.

18. Fraker, C. A.; Alvarez, S.; Papadopoulos, P.; Giraldo, J.; Gu, W.; Ricordi, C.; Inverardi, L.; Dominguez-Bendala, J. Enhanced oxygenation promotes beta-cell differentiation in vitro. Stem Cells 25(12):3155-3164; 2007.

19. Giuliani, M.; Moritz, W.; Bodmer, E.; Dindo, D.; Kugelmeier, P.; Lehmann, R.; Gassmann, M.; Groscurth, P.; Weber, M. Central necrosis in isolated hypoxic human pancreatic islets: evidence for postisolation ischemia. Cell Transplant. 14(1):67-76; 2005.

20. Glicklis, R.; Merchuk, J. C.; Cohen, S. Modeling mass transfer in hepatocyte spheroids via cell viability, spheroid size, and hepatocellular functions. Biotechnol. Bioeng. 86(6):672-680; 2004.

21. Heinis, M.; Simon, M. T.; Ilc, K.; Mazure, N. M.; Pouyssegur, J.; Scharfmann, R.; Duvillie, B. Oxygen tension regulates pancreatic beta-cell differentiation through hypoxiainducible factor 1 alpha. Diabetes 59(3):662-669; 2010.

22. Heizmann, O.; Loehe, F.; Volk, A.; Schauer, R. J. Ischemic preconditioning improves postoperative outcome after liver resections: a randomized controlled study. Eur. J. Med. Res. 13(2):79-86; 2008.

23. Hogan, A. R.; Doni, M.; Ribeiro, M. M.; Molano, R. D.; Cobianchi, L.; Molina, J.; Zahr, E.; Ricordi, C.; Pastori, R. L.; Pileggi, A. Ischemic preconditioning improves islet recovery after pancreas cold preservation. Transplant. Proc. 41(1):354-355; 2009.

24. Ichii, H.; Inverardi, L.; Pileggi, A.; Molano, R. D.; Cabrera, O.; Caicedo, A.; Messinger, S.; Kuroda, Y.; Berggren, P. O.; Ricordi, C. A novel method for the assessment of cellular composition and beta-cell viability in human islet preparations. Am. J. Transplant. 5(7):1635-1645; 2005.

25. Ijaz, A.; Tejada, T.; Catanuto, P.; Xia, X.; Elliot, S. J.; Lenz, O.; Jauregui, A.; Saenz, M. O.; Molano, R. D.; Pileggi, A.; Ricordi, C.; Fornoni, A Inhibition of C-jun N-terminal kinase improves insulin sensitivity but worsens albuminuria in experimental diabetes. Kidney Int. 75(4): 381-8; 2008.

26. Ilieva, A.; Yuan, S.; Wang, R. N.; Agapitos, D.; Hill, D. J.; Rosenberg, L. Pancreatic islet cell survival following islet isolation: the role of cellular interactions in the pancreas. J. Endocrinol. 161(3):357-364; 1999.

27. Jansson, L. The regulation of pancreatic islet blood flow. Diabetes Metab. Rev. 10(4):407-416; 1994.

28. Kajimoto, Y.; Kaneto, H. Role of oxidative stress in pancreatic beta-cell dysfunction. Ann. N. Y. Acad. Sci. 1011: 168-176; 2004.

29. Kaneto, H.; Kajimoto, Y.; Fujitani, Y.; Matsuoka, T.; Sakamoto, K.; Matsuhisa, M.; Yamasaki, Y.; Hori, M. Oxidative stress induces p21 expression in pancreatic islet cells: possible implication in beta-cell dysfunction. Diabetologia 42(9):1093-1097; 1999.

30. Kaneto, H.; Katakami, N.; Kawamori, D.; Miyatsuka, T.; Sakamoto, K.; Matsuoka, T. A.; Matsuhisa, M.; Yamasaki, Y. Involvement of oxidative stress in the pathogenesis of diabetes. Antioxid. Redox Signal. 9(3):355-366; 2007.

31. Kapturczak, M. H.; Flotte, T.; Atkinson, M. A. Adenoassociated virus (AAV) as a vehicle for therapeutic gene delivery: improvements in vector design and viral production enhance potential to prolong graft survival in pancreatic islet cell transplantation for the reversal of type 1 diabetes. Curr. Mol. Med. 1(2):245-258; 2001.

32. Kazzaz, J. A.; Horowitz, S.; Li, Y.; Mantell, L. L. Hyperoxia in cell culture. A nonapoptotic programmed cell death. Ann N Y. Acad. Sci. 887:164-170; 1999.

33. Klein, D.; Mendoza, V.; Pileggi, A.; Molano, R. D.; Barbe-Tuana, F. M.; Inverardi, L.; Ricordi, C.; Pastori, R. L. Delivery of TAT/PTD-fused proteins/peptides to islets via pancreatic duct. Cell Transplant. 14(5):241-248; 2005.

34. Ko, S. H.; Ryu, G. R.; Kim, S.; Ahn, Y. B.; Yoon, K. H.; Kaneto, H.; Ha, H.; Kim, Y. S.; Song, K. H. Inducible nitric oxide synthase-nitric oxide plays an important role in acute and severe hypoxic injury to pancreatic beta cells. Transplantation 85(3):323-330; 2008.

35. London, N. J.; Swift, S. M.; Clayton, H. A. Isolation, culture and functional evaluation of islets of Langerhans. Diabetes Metab. 24(3):200-207; 1998.

36. Malda, J.; Klein, T. J.; Upton, Z. The roles of hypoxia in the in vitro engineering of tissues. Tissue Eng. 13(9):2153-2162; 2007.

37. Mates van Lobensels, E.; Anderson, J. C.; Hildebrandt, J.; Hlastala, M. P. Modeling diffusion limitation of gas exchange in lungs containing perfluorocarbon. J. Appl. Physiol. 86(1):273-284; 1999.

38. McCabe, C.; O'Brien, T. The rational design of beta cell cytoprotective gene transfer strategies: targeting deleterious iNOS expression. Mol. Biotechnol. 37(1):38-47; 2007.

39. Moritz, W.; Meier, F.; Stroka, D. M.; Giuliani, M.; Kugelmeier, P.; Nett, P. C.; Lehmann, R.; Candinas, D.; Gassmann, M.; Weber, M. Apoptosis in hypoxic human pancreatic islets correlates with HIF-alpha expression. Faseb J. 16(7):745-747; 2002.

40. Murry, C. E.; Jennings, R. B.; Reimer, K. A. Preconditioning with ischemia: a delay of lethal cell injury in ischemic myocardium. Circulation 74(5):1124-1136; 1986.

41. Papas, K. K.; Avgoustiniatos, E. S.; Tempelman, L. A.; Weir, G. C.; Colton, C. K.; Pisania, A.; Rappel, M. J.; Friberg, A. S.; Bauer, A. C.; Hering, B. J. High-density culture of human islets on top of silicone rubber membranes. Transplant. Proc. 37(8):3412-3414; 2005.
42. Papas, K. K.; Long, R. C., Jr.; Constantinidis, I.; Sambanis, A. Effects of oxygen on metabolic and secretory activities of beta TC3 cells. Biochim. Biophys. Acta 1291(2): 163-166; 1996.
43. Pileggi, A.; Molano, R. D.; Berney, T.; Cattan, P.; Vizzardelli, C.; Oliver, R.; Fraker, C.; Ricordi, C.; Pastori, R. L.; Bach, F. H.; Inverardi, L. Heme oxygenase-1 induction in islet cells results in protection from apoptosis and improved in vivo function after transplantation. Diabetes 50(9):1983-1991; 2001.
44. Reimer, K. A.; Murry, C. E.; Yamasawa, I.; Hill, M. L.; Jennings, R. B. Four brief periods of myocardial ischemia cause no cumulative ATP loss or necrosis. Am. J. Physiol. 251(6 Pt 2):H1306-1315; 1986.
45. Ribeiro, M. M.; Klein, D.; Pileggi, A.; Molano, R. D.; Fraker, C.; Ricordi, C.; Inverardi, L.; Pastori, R. L. Heme oxygenase-1 fused to a TAT peptide transduces and protects pancreatic beta-cells. Biochem. Biophys. Res. Commun. 305(4):876-881; 2003.
46. Ricordi, C.; Fraker, C.; Szust, J.; Al-Abdullah, I.; Poggioli, R.; Kirlew, T.; Khan, A.; Alejandro, R. Improved human islet isolation outcome from marginal donors following addition of oxygenated perfluorocarbon to the cold-storage solution. Transplantation 75(9):1524-1527; 2003.
47. Ricordi, C.; Strom, T. B. Clinical islet transplantation: advances and immunological challenges. Nat. Rev. Immunol. 4(4):259-268; 2004.
48. Robertson, R. P.; Harmon, J. S. Diabetes, glucose toxicity, and oxidative stress: A case of double jeopardy for the pancreatic islet beta cell. Free Radic. Biol. Med. 41(2): 177-184; 2006.
49. Shapiro, A. M.; Lakey, J. R.; Ryan, E. A.; Korbutt, G. S.; Toth, E.; Warnock, G. L.; Kneteman, N. M.; Rajotte, R. V. Islet transplantation in seven patients with type 1 diabetes mellitus using a glucocorticoid-free immunosuppressive regimen. N. Engl. J. Med. 343(4):230-238; 2000.
50. Tiedge, M.; Lortz, S.; Drinkgern, J.; Lenzen, S. Relation between antioxidant enzyme gene expression and antioxidative defense status of insulin-producing cells. Diabetes 46(11):1733-1742; 1997.

Example 11

Examples of Fluorocarbon Derivatives

The fluorocarbon derivatives described herein include, among other compounds, which include but are not limited to fluoropolymers, refrigerants, solvents, anesthetics, fluorosurfactants, fluorinated silanes and partially fluorinated silanes.

Fluorocompounds are also encompassed by the devices and methods described herein. Fluorocompounds include any molecule with fluorine bound to a carbon chain that is not a perfluorocarbon in which all the hydrogens that were part of a carbon chain are replaced by fluorine atoms and having a side group that is not fluorine. A specific example of a fluorocompound includes but is not limited to a fluorinated or partially fluorinated alkyl silane, particularly 1H, 1H, 2H, 2H perfluorooctyl triethoxy silane as it is a fluorinated carbon chain tail group on a backbone made up of silicon, carbon and oxygen (triethoxysilane). The structure of silane is shown below.

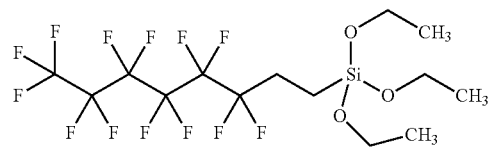 [SMILES: CCO[Si](CCC(F)(F)C(F)(F)C(F)(F)C(F)(F)C(F)(F)C(F)(F)F)(OCC)OCC]

Silanes are typically silicon with 4 hydrogens, in the most simple form. In a typical embodiment of the devices and methods described herein, the silane is triethoxy (the O—CH3 groups) and then it is fluorinated because the fluorocarbon derivative chain replaces the last hydrogen, which with the hydrogen would make it triethoxysilane, instead of perfluorotriethoxysilane. The structure of triethoxy silane is as follows:

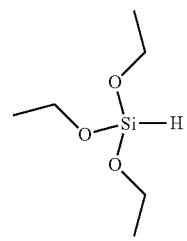

As an example of one embodiment of a fluorocarbon derivative matrix, PDMS is mixed, combined or impregnated with a fluorocarbon derivative and formed into a gas permeable/liquid impermeable membrane. The fluorocarbon derivatives described herein may be used in any suitable form, and may be combined or mixed with a silicone composition using any suitable methodology. For example, fluorocarbon derivative (e.g., a fluorinated silane or partially fluorinated silane) may be in a cross-linked form before combing with, mixing with, or impregnating a silicone composition. Additionally, a fluorocarbon derivative (e.g., a fluorinated silane or partially fluorinated silane) may be cross-linked with a silicone composition.

In one embodiment, a cell and tissue culture apparatus includes a tissue culture device containing a gas permeable, liquid impermeable membrane barrier, the gas permeable, liquid impermeable membrane comprising a silicone composition impregnated, mixed or combined with a fluorocarbon derivative; support members extending from the bottom, side or top of the tissue culture device to elevate the tissue culture device to allow air flow; and, a tray or culture flask comprising the tissue culture device, wherein the liquid impermeable membrane barrier defines a continuous surface of the tissue culture device and allows oxygenation of and minimization of hypoxia in cells resting thereupon. The fluorocarbon derivative can be a fluorosilane, e.g., triethoxyfluorosilane. In some embodiments, the fluorocarbon derivative is homogenously dispersed throughout the silicone composition. Typically, the tissue culture apparatus comprises an upper and lower opening, and the barrier defines a continuous bottom surface of the tissue culture device. The liquid impermeable membrane barrier can further include at least one material selected from ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels. In some embodiments, the fluorocarbon derivative and silicone composition has a ratio of between about 0.001% v/v fluorocarbon derivative per ml of composition up to 80% v/v fluorocarbon derivative per ml of silicone composition (e.g., a ratio of about 10% to 20% v/v fluorocarbon derivative per ml of silicone composition). The tray is made from at least one material comprising ceramics, polymers, woven substrates, non-woven substrates, polyamide, polyester, polyurethane, fluorocarbon polymers, polyethylene, polypropylene, perfluorinated hydrocarbon, polyvinyl alcohol, polystyrene, vinyl, plastics, metals, alloys, minerals, non-metallic minerals, wood, fibers, cloth, glass, hydro gels and silicone. The tray can include a plurality of tissue culture devices, as well as a lid which allows for gaseous exchange. Using the cell and tissue culture apparatus, the oxygenation and minimization of hypoxia increases proliferation of the cells in some embodiments, and in other embodiments, increases differentiation of the cells. Examples of cells to be cultured include neural stem cells, beta cells and hepatocytes.

An apparatus for the transportation of cells, tissues and organs includes a culture device containing a gas permeable, liquid impermeable membrane barrier to allow air flow, the gas permeable, liquid impermeable membrane comprising a silicone composition impregnated, mixed or combined with a fluorocarbon derivative, wherein the liquid impermeable membrane barrier defines a continuous surface of at least one side of the culture device and allows oxygenation of and minimization of hypoxia in cells resting thereupon; and, a container enclosing the culture device.

In one embodiment, of a method of growing cells or tissue explants in an enhanced oxygen delivery tissue culture apparatus, the method includes suspending the cells or tissue explants to be cultured in an apparatus as described herein, in an appropriate amount of tissue culture medium to form a suspension; and incubating the cell culture apparatus, containing the suspension of medium and cells, in a cell culture incubator. Cells to be cultured can be anchorage-dependent cells or anchorage-independent cells. The cells can be any type of cells, including stem cells, for example.

Other Embodiments

It is to be understood that while the invention has been described in conjunction with the detailed description thereof, the foregoing description is intended to illustrate and not limit the scope of the invention. Other aspects, advantages, and modifications are within the scope of the following claims.

All references cited herein, are incorporated herein by reference.

What is claimed is:

1. A cell and tissue culture apparatus comprising:
a tissue culture device containing a gas permeable, liquid impermeable membrane barrier, the gas permeable, liquid impermeable membrane comprising a silicone composition impregnated, mixed or combined with a fluorocarbon derivative; support members extending from the bottom, side or top of the tissue culture device to elevate the tissue culture device to allow air flow; and, a tray or culture flask comprising the tissue culture device, wherein the liquid impermeable membrane barrier defines a continuous surface of the tissue culture device and allows oxygenation of and minimization of hypoxia in cells resting thereupon.

2. The cell and tissue culture apparatus of claim 1, wherein the fluorocarbon derivative is fluorosilane.

3. The cell and tissue culture apparatus of claim 2, wherein the fluorosilane is triethoxyfluorosilane.

4. The cell and tissue culture apparatus of claim 1, wherein the tissue culture apparatus comprises an upper and lower opening; and wherein the barrier defines a continuous bottom surface of the tissue culture device.

5. The cell and tissue culture apparatus of claim 1, wherein the liquid impermeable membrane barrier further comprises at least one material selected from ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels.

6. The cell and tissue culture apparatus of claim 1, wherein the fluorocarbon derivative and silicone composition has a ratio of between about 0.001% v/v fluorocarbon derivative per ml of composition up to 80% v/v fluorocarbon derivative per ml of silicone composition.

7. The cell and tissue culture apparatus of claim 6, wherein the fluorocarbon derivative and silicone composition has a ratio of about 10% to 20% v/v fluorocarbon derivative per ml of silicone composition.

8. The cell and tissue culture apparatus of claim 1, wherein the tray is made from at least one material comprising ceramics, polymers, woven substrates, non-woven substrates, polyamide, polyester, polyurethane, fluorocarbon polymers, polyethylene, polypropylene, perfluorinated hydrocarbon, polyvinyl alcohol, polystyrene, vinyl, plastics, metals, alloys, minerals, non-metallic minerals, wood, fibers, cloth, glass, hydro gels and silicone.

9. The cell and tissue culture apparatus of claim 1, wherein the tray comprises a plurality of tissue culture devices.

10. The cell and tissue culture apparatus of claim 1, wherein the tray comprises a lid which allows for gaseous exchange.

11. The cell and tissue culture apparatus of claim 1, wherein the oxygenation and minimization of hypoxia increases proliferation of the cells.

12. The cell and tissue culture apparatus of claim 1, wherein the oxygenation and minimization of hypoxia increases differentiation of the cells.

13. The cell and tissue culture apparatus of claim 1, wherein the cells are selected from the group consisting of: neural stem cells, beta cells and hepatocytes.

14. The cell and tissue culture apparatus of claim 1, wherein the fluorocarbon derivative is homogenously dispersed throughout the silicone composition.

15. A method of growing cells or tissue explants in an enhanced oxygen delivery tissue culture apparatus, the method comprising: suspending the cells or tissue explants to be cultured in the apparatus according to claim 1, in an appropriate amount of tissue culture medium to form a suspension; and incubating the cell culture apparatus, containing the suspension of medium and cells, in a cell culture incubator.

16. The method of claim 15, wherein the cells to be cultured are anchorage-dependent cells.

17. The method of claim 15, wherein the cells to be cultured are anchorage-independent cells.

18. The method of claim 15, wherein the cells are stem cells.

19. An apparatus for the transportation of cells, tissues and organs comprising:
a culture device containing a gas permeable, liquid impermeable membrane barrier to allow air flow, the gas permeable, liquid impermeable membrane comprising a silicone composition impregnated, mixed or combined with a fluorocarbon derivative, wherein the liquid impermeable membrane barrier defines a continuous surface of at least one side of the culture device and allows oxygenation of and minimization of hypoxia in cells resting thereupon; and,
a container enclosing the culture device.

* * * * *